United States Patent
Lub et al.

(10) Patent No.: US 10,329,482 B2
(45) Date of Patent: Jun. 25, 2019

(54) CLASS OF ORGANIC PHOSPHORS BASED ON DERIVATIVES OF BENZIMIDAZOXANTHENOISOQUINOLINONE FOR LED LIGHTING

(71) Applicant: SIGNIFY HOLDING B.V., Eindhoven (NL)

(72) Inventors: Johan Lub, Valkenswaard (NL); Paulus Albertus Van Hal, Waalre (NL); Rifat Ata Mustafa Hikmet, Eindhoven (NL); Sylvain Loic Jean-Luc Hamon, Groningen (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 61 days.

(21) Appl. No.: 15/521,095

(22) PCT Filed: Oct. 19, 2015

(86) PCT No.: PCT/EP2015/074126
§ 371 (c)(1),
(2) Date: Apr. 21, 2017

(87) PCT Pub. No.: WO2016/062657
PCT Pub. Date: Apr. 28, 2016

(65) Prior Publication Data
US 2018/0016491 A1    Jan. 18, 2018

(30) Foreign Application Priority Data

Oct. 21, 2014   (WO) ................. PCT/EP2014/072560
Feb. 10, 2015   (EP) ..................................... 15154537

(51) Int. Cl.
*C09K 11/02* (2006.01)
*C09K 11/06* (2006.01)
(Continued)

(52) U.S. Cl.
CPC ............ *C09K 11/06* (2013.01); *C07D 247/00* (2013.01); *C07D 491/16* (2013.01);
(Continued)

(58) Field of Classification Search
CPC ............ C09K 11/06; C09K 2211/1048; C09K 2211/1088; C09K 11/025;
(Continued)

(56) References Cited

U.S. PATENT DOCUMENTS 6,046,335 A *  4/2000  Boeglin ............... C07D 471/14
                                                    106/31.77
6,537,679 B1  3/2003  Buoni et al.
2015/0054401 A1 * 2/2015  Van Bommel ......... H05B 33/14
                                                    313/504

FOREIGN PATENT DOCUMENTS

CN       103930517 A    7/2014
DE        2328727 A1    1/1975
(Continued)

OTHER PUBLICATIONS

Xuhong Qian, et al., "A Study on the Relationship Between Stoke's Shift and Low Frequency Half-Value Component of Fluorescent Compounds," Dyes and Pigments, vol. 32, No. 4 1996 (7 Pages).
(Continued)

Primary Examiner — William F Kraig
Assistant Examiner — Vicki B. Booker
(74) Attorney, Agent, or Firm — Akarsh P. Belagodu

(57) ABSTRACT

The invention provides a lighting device including a light source configured to generate light source light and a light converter configured to convert at least part of the light source light into visible converter light. The light converter includes a matrix containing a luminescent material based on derivatives of benzimidazoxanthenoisoquinolinone. The lighting device may include a further luminescent material.

13 Claims, 20 Drawing Sheets

(51) Int. Cl.
*H01L 33/50* (2010.01)
*H01L 51/00* (2006.01)
*H05B 33/14* (2006.01)
*C07D 247/00* (2006.01)
*C07D 491/16* (2006.01)
*G02F 1/1335* (2006.01)

(52) U.S. Cl.
CPC ............ *C09K 11/025* (2013.01); *H01L 33/50* (2013.01); *H01L 33/502* (2013.01); *H01L 51/0053* (2013.01); *H01L 51/0071* (2013.01); *H01L 51/0072* (2013.01); *H05B 33/14* (2013.01); *C09K 2211/1018* (2013.01); *C09K 2211/1044* (2013.01); *C09K 2211/1048* (2013.01); *C09K 2211/1088* (2013.01); *G02F 1/133621* (2013.01); *G02F 2001/133614* (2013.01)

(58) Field of Classification Search
CPC .... C09K 2211/1018; C09K 2211/1044; H01L 33/50; H01L 51/0053; H01L 51/0072; H01L 51/0071; H01L 33/502; C07D 247/00; C07D 491/16; H05B 33/14; G02F 2001/133614; G02F 1/133621

See application file for complete search history.

(56) References Cited

FOREIGN PATENT DOCUMENTS

| | | |
|---|---|---|
| EP | 2645822 A1 | 2/2013 |
| JP | 06228549 | 8/1994 |
| WO | 2011031871 A1 | 3/2011 |
| WO | 2014131628 A1 | 9/2014 |

OTHER PUBLICATIONS

Qian Xuhong, et al., "Benzoxanthene-3,4-Dicarboximides and Benzimidazoxanthenoisoquinolinones," J. Chem. Eng. Data 1988 (2 Pages).

* cited by examiner

+

CLASS OF ORGANIC PHOSPHORS BASED ON DERIVATIVES OF BENZIMIDAZOXANTHENOISOQUINOLINONE FOR LED LIGHTING

CROSS-REFERENCE TO PRIOR APPLICATIONS

This application is the U.S. National Phase application under 35 U.S.C. § 371 of International Application No. PCT/EP2015/074126, filed on Oct. 19, 2015, which claims the benefit of European Patent Application No. PCT/EP2014/072560, filed on Oct. 21, 2014 and European Patent Application No. 15154537.3, filed on Feb. 10, 2015. These applications are hereby incorporated by reference herein.

FIELD OF THE INVENTION

The invention relates to a lighting device comprising (a) a light source configured to generate light source light, and (b) a light converter configured to convert at least part of the light source light into visible converter light. The invention further pertains to such light converter per se as well as to a luminescent material that can be comprised by such light converter.

BACKGROUND OF THE INVENTION

Phosphor-enhanced light sources are known per se and are used for substantially all kinds of light sources. Phosphor-enhanced light sources comprise a light emitter and a luminescent material. The luminescent material is arranged for converting at least part of the light emitted by the light emitter into light of a longer wavelength.

Well-known phosphor-enhanced light sources are, for example, mercury vapor discharge lamps in which the light is emitted from a discharge in which the presence of mercury vapor causes the discharge to emit ultraviolet radiation. At least a part of the ultraviolet radiation is absorbed by a luminescent material and converted into light of a longer wavelength which is subsequently emitted by the luminescent material. Such mercury vapor discharge lamp may, for example, comprise a discharge vessel in which the discharge is generated. The luminescent material is typically applied to the inner wall of the discharge vessel such that the ultraviolet radiation emitted by the discharge does not need to pass the discharge vessel but is inside the discharge vessel converted into, for example, visible light.

Alternatively, the phosphor-enhanced light source may comprise a solid-state light emitter as the light emitter. Such a solid-state light emitter may, for example, be a light emitting diode, or a laser diode, or an organic light emitting diode. The light emitted by a solid-state light emitter typically has a relatively narrow spectrum arranged around a center wavelength. The width of the spectrum may, for example, be defined by the Full Width Half Maximum (further also indicated as FWHM) of the emission peak which is a width of the emission peak measured at an intensity being half the maximum emission intensity of the light emitted by the solid-state light emitter. The FWHM of a typical emission spectrum of the solid-state light emitter is less than 30 nanometer, which is typically identified by the human eye as light of a single color.

To change the color of the light emitted by the solid-state light emitter, luminescent materials may be added to generate a phosphor-enhanced light source. The luminescent material may, for example, be applied as a layer on top of the (LED) die of the solid-state light emitter, or may, for example, be dispersed in a matrix which may be located at a distance of the solid-state light emitter, a so called "remote phosphor" arrangement. The luminescent material may also be part of a mixture of different luminescent materials, for example, each generating a different color such that the mixed light, for example, generates white light having a specific color temperature. Furthermore, luminescent materials may be added to solid-state light emitters to improve the color rendering characteristics of the solid-state light emitters, as the typical emission characteristic of the luminescent materials is a relatively broad spectrum of light.

The use of dyes in matrices is (also) known in the art. U.S. Pat. No. 6,537,679, for instance, describes a fluorescent retro reflective article comprising a polymer resin comprising poly(1,4-cyclohexanedimethanol-co-ethylene terephthalate) (PETG) and a fluorescent dye selected from the group consisting of perylene imide and perylene ester dyes, thioxanthene dyes, benzoxanthene dyes, and benzothiazine dyes. The PETG fluorescent resin matrix can be used to enhance daytime visibility of a roadway marker. Such a pavement marker comprises a base member comprising a structure of a light-transmissible fluorescent material, the structure having a top surface and a front edge surface, the base member being configured to provide an air cap beneath the structure.

Qian Xuhong et al. (J. Chem. Eng. Data (1988, 33, 528-529) describes some benzoxanthene-3,4-dicarboximides and benzimidazoxanthenoisoquinolinones, and their physical and spectral data. JP06228549 describes an organic electroluminescent element with a compound as described by Qian Xuhong et al. EP2645822 describes a lighting device comprising a light source and luminescent materials. The luminescent materials comprising a first organic luminescent material, a second organic luminescent material, optionally one or more further organic luminescent materials, and optionally one or more further inorganic luminescent materials. The light source and the luminescent materials are configured to generate white lighting device light during operation. The first organic luminescent material degrades with time, the second organic luminescent material degrades with time, and the optional one or further organic luminescent materials degrade with time. The luminescent materials are configured to maintain the lighting device light white during operation time of the lighting device. Xuhong Qian et al. (Dyes and Pigments, vol. 32, no. 4, p. 229-235 (1996)) provides a study on the relationship between Stokes shift and low frequency halve-value component of fluorescent compounds, amongst others one described by Qian Xuhong et al.

DE 2328727 describes water-insoluble dyes having a general formula (I) or (II) related to formulas 1A and 1B as described in the present application, with at the O-position a group indicated with X, wherein X is O or S, and wherein some specific side groups denote H, C2H5, an acyl or alkoxy, and some other specific side groups denote H or non-ionogenic substituents; with the proviso that two adjacent groups may form an aromatic or heteroaromatic ring). These compounds can be produced e.g. by internally cyclizing the corresponding diazonium salts (to form the ring containing X). These dyes are suitable for cellulose acetate, polyester, or polyamide textiles, articles made from polystyrene, polymethyl methacrylate, PVC, polycarbonates, polyethylene, polypropylene and super polyamides, and for the production of pigments for lacquers or printing pastes. Bright, clear, fluorescent yellow to red colors fast to light, etc., are obtained.

SUMMARY OF THE INVENTION

Efficiency of white emitting light solid state light sources can still be improved. This can be best done by combining RGB LEDs. However, green LEDs are presently not efficient enough in order to obtain high efficiencies. For this reason, phosphor converted (PC) LEDs are suggested for obtaining white light. With the blue LED's as primary source a red and yellow luminescent phosphors are needed. These phosphors should be stable under blue light irradiation conditions during the lifetime of the complete light source (for example TL-retrofit tube, operating at elevated temperature, lifetime of at least 50.000 hours).

The use of yellow organic phosphors (see e.g. also EP2645822) derived from perylene, such as F170 (CAS: 936212-95-2) or F83 (CAS: 100443-95-6), and of Solvent Yellow 98 (CAS: 12671-74-8) or fluorescent yellow 43 (CAS: 19125-99-6), results in low lifetimes. These yellow phosphors degrade too fast for use in lighting applications.

Hence, it is an aspect of the invention to provide an alternative lighting device, and especially an alternative light converter, which preferably further at least partly obviate one or more of above-described drawbacks. It is further an aspect of the invention to provide an alternative luminescent material, especially emitting in the green and/or yellow, especially for combination with a blue light source, such as a blue LED, which preferably further at least partly obviates one or more of above-described drawbacks.

It was surprisingly found that derivatives of 8H-benzo[3,4]isochromeno[7,8,1-def]benzo[4,5]imidazo[1,2-b]isoquinolin-8-one exhibit much longer lifetimes under the irradiation conditions than known similar prior art systems. Mixtures of derivatives of the two isomers namely 8H-benzo[3,4]isochromeno[7,8,1-def]benzo[4,5]imidazo[1,2-b]isoquinolin-8-one (2410A) and 7H-benzo[3,4]isochromeno[7,8,1-def]benzo[4,5]imidazo[2,1-a]isoquinolin-7-one (2410B) in approximately equimolar ratio were obtained. Lifetime increased up to 20 Khr were obtained with these mixtures. However, the quantum efficiency of these dye mixtures was relatively low; not exceeding 0.8.

It was further surprisingly found after separation of the two isomers from the mixture that the one derived from structure 2410A has excellent spectral properties in the yellow region and a high quantum yield, exceeding 0.9 (90% quantum efficiency). The other isomer derived from 2410B exhibits an emission in the orange region with a relatively low quantum yield. Thus the use of the first isomer leads to lamps with higher efficiency. Further, it appears that 8H-benzo[3,4]isochromeno[7,8,1-def]benzo[4,5]imidazo[1,2-b]isoquinolin-8-one or a derivative thereof has substantially better optical properties than the isomer 7H-benzo[3,4]isochromeno[7,8,1-def]benzo[4,5]imidazo[2,1-a]isoquinolin-7-one, and derivatives thereof.

In a specific embodiment, the phosphor is in the remote phosphor configuration which may lead to a total increase in the system efficacy. This configuration is most suitable in low power low operating temperature applications such as TLED (tube LED configuration, e.g. LEDs implement in a T8 tube (known in the art of fluorescent lighting) or other tubular configurations). However, other type of applications, such as directly on the solid state light source die may also be possible.

Hence, in a first aspect, the invention provides a lighting device comprising (a) a light source configured to generate light source light, (b) a light converter configured to convert at least part of the light source light into visible converter light, wherein the light converter comprises a (polymeric) matrix containing a luminescent material, the luminescent material comprising an organic phosphor defined by formula IA:

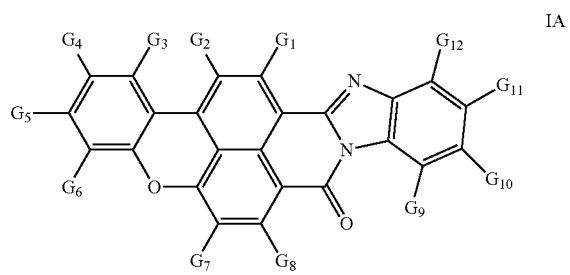

IA wherein G1-G12 are independently selected from hydrogen, halogen, R1, OR1, NHR1, and NR2R1, wherein R1 and R2 are independently selected from C1-C18alkyl, C6-C24aryl, and C6-C24 heteroaryl. Hence, in a specific embodiment G1-G12 are independently selected from hydrogen, halogen, R1, OR1, NHR1, and NR2R1, wherein R1 and R2 are independently selected from C1-C18alkyl, C6-C24aryl, and C6-C24 heteroaryl. Further, one or more of the G1-G12 groups may independently have covalent bindings or links with a matrix when embedded in a matrix.

Separation of the isomers may e.g. be done via column chromatography or selective crystallization, techniques known in the art.

Especially, G1-G12 are independently selected from hydrogen, halogen, R1, OR1, NHR1, and NR2R1, wherein R1 and R2 are independently selected from C1-C18alkyl, C6-C24aryl, and C6-C24 heteroaryl, wherein optionally one or more of G1-G12 is covalently linked to the matrix, and wherein when the organic phosphor defined by formula IB (see below) is available in the luminescent material, the phosphor defined by formula IB and the phosphor defined by formula IA have a molar ratio of 1B/1A≤05, especially ≤0.1. Such organic phosphors provide best optical results in terms of quantum efficiency and/or stability under radiation (while being embedded in a matrix).

Optionally, the organic phosphor comprises a combination of two organic phosphors, i.e. the organic phosphor IA as indicated above and its isomer,

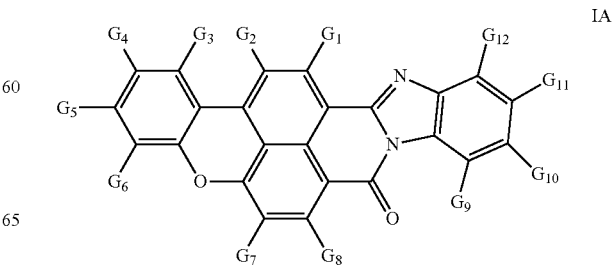

IA

-continued

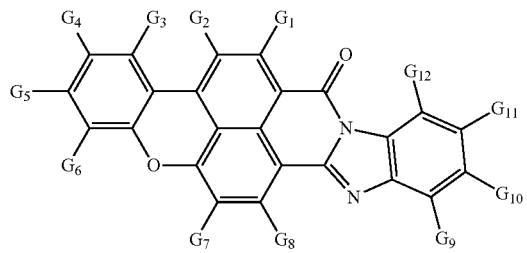

IB but the two isomers having a molecular ratio of the first organic phosphor IA to the second organic phosphor IB in the ratio of 1.1 and larger, such as in the ratio range of 2-1000. Hence, when the phosphor (or luminescent material) comprises both phosphor IA and 1B, the molar ratio of IB/IA is ≤0.5, such as ≤0.1, such as 0.05 or smaller, like ≤0.01, like ≤0.001, for instance in the range of 0.5-0.001, like 0.1-0.001. The isomers may spectroscopically be distinguished or LCMS (liquid chromatography-mass spectrometry) may be applied to distinguish the isomers IA and IB.

In a further aspect, the invention also provides a light converter per se. Hence, in a further aspect the invention also provides a light converter comprising a matrix containing the luminescent material comprising the organic phosphor. As will be elucidated below, such matrix may also comprise one or more further luminescent materials, like quantum dot based materials and/or nitride based materials, and/or other luminescent materials, etc., that may especially luminesce in the red.

In yet a further aspect, the invention also provides such luminescent material per se. Hence, in a further aspect, the invention also provides a luminescent material comprising the organic phosphor according to formula IA, optionally in combination with a and IB (as defined above), but with the former in molecular excess relative to the latter. Hence, in an aspect the invention provides luminescent material comprising at least an organic phosphor defined by formula IA and optionally (the luminescent material) also (comprises) an organic phosphor defined by formula IB, wherein G1-G12 are independently selected from hydrogen, halogen, R1, OR1, NHR1, and NR2R1, wherein R1 and R2 are independently selected from C1-C18alkyl, C6-C24aryl, and C6-C24 heteroaryl, and wherein when the organic phosphor defined by formula IB is (also) available in the luminescent material, the phosphor defined by formula IB and the phosphor defined by formula IA have a molar ratio of 1B/1A≤0.5, especially ≤0.1, and wherein especially one or more of G2 and G7 comprises independently a group selected from the group consisting of R1, OR1, NHR1, and NR2R1, even more especially selected from the group consisting of R1 and OR1.

As indicated above, it appeared surprisingly that the benzimidazoxanthenoisoquinolinone derivative of formula IA has a relative higher quantum efficiency, especially higher than its IB isomer, and also higher than some other organic phosphors known in the art, while having a good lifetime under e.g. blue light irradiation. Further, these materials appear to have relative high quantum efficiencies. Also, high color rendering indexes in combination with a source of blue light, like a blue LED, and optionally a source of one or more of green, yellow and red light, such as a red organic luminescent material and/or red inorganic luminescent material, such as a nitride or quantum dots, may provide white light with a CRI of at least 80 such as at least 84, even more at least 88, like at least 92.

In a specific embodiment at least four of G1-G12 for the organic phosphor IA (and when the organic phosphor IB is present, also for this phosphor) (independently), are H. Even more especially, all G1-G12 for the organic phosphor IA, or of the organic phosphor IA (and optionally organic phosphor IB), are H. In general, due to the synthesis procedure, $G_n$ of phosphor IA is the same as $G_n$ of phosphor IB (i.e. G1 (IA)=G1 (IB); G2 (IA)=G2 (IB); G3 (IA)=G3 (IB); etc. etc.). Note that the phrase "all G1-G12 for the organic phosphor IA are H" may still include that one or more of G1-G12, but not all, and especially only one of G1-G12 may be a covalent link with a matrix (when embedded in a matrix). The hydrogen substituted benzimidazoxanthenoisoquinolinone derivatives appear to have good stability and interesting optical properties such as a (blue)green emission that is tunable from the blue to the green, and even up to yellow or even red, dependent upon the substituents. Further, these phosphors are well excitable in blue, have a relative high efficiency (in solution up to 95%), and, as indicated above, a relative high stability. The addition of non-H substituents allows a tuning of the emission. Hence, emission ranges can be obtained where prior art organic dyes may emit, but where the present dye according to formula 1A may be substantially more stable and/or more efficient (QE).

Especially, one of more of G1-G12 is not H, especially G2 and/or G7 is not H. In yet another embodiment, especially one of more of G1-G12 is not $OCH_3$, especially G2 and/or G7 is not $OCH_3$. In even a further specific embodiment, one or more of G2 and G7 comprises a phenyl group (see also below); this may even further increase stability.

In yet a further specific embodiment, one or more of G1-G12 of the organic phosphor IA (and optionally IB), especially one or more of G2 and G7, are independently selected from R1, OR1, NHR1, and NR2R1, wherein one or more of R1 and R2 independently comprise a group defined by formula II:

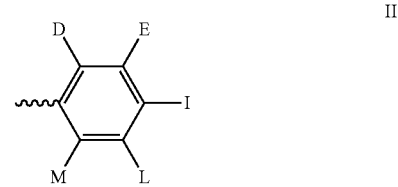

II wherein D, E, I, L and M are independently selected from hydrogen, halogen, R3, OR3, NHR3, and NR4R3, and wherein R3 and R4 are independently selected from C1-C18alkyl, C6-C24aryl, and C6-C24 heteroaryl.

Optionally, one or more, especially only one of D, E, I, L and M may include a covalent link with a matrix.

Especially, at least two of D, E, I, L and M are H, even more especially all are H. With such groups or substituents, the emission may shift more in the green-yellow, relative to phosphors having formula IA (or IB) with only H substituents. Good results are obtained when at least ten of G1-G12 independently are H. Especially, only one or two of G1-G2, for the phosphor having formula IA (and optionally IB), are independently selected from R1, OR1, NHR1, and NR2R1, wherein one or more of R1 and R2 independently comprise a group defined by formula II.

In yet a further specific embodiment, independently one or more of G2 and G7 for the organic phosphors IA (and optionally IB) comprise R1 or OR1, especially R1, with R1 being a substituent according to formula II, wherein especially D, E, I, L and M are H, and wherein at least four, especially all, of G1, G3, G4, G5, G6, G8, G9, G10, G11 and G12 independently are H. Additionally or alternatively, independently one or more of G2 and G7 for the organic phosphor IA (and optionally IB) comprise OR1, with R1 being a substituent according to formula II, wherein especially D, E, I, L and M are H, and wherein especially at least four, especially all, of G1, G3, G4, G5, G6, G8, G9, G10, G11 and G12, even more especially all, independently are H. Especially good results are obtained when at least eight of G1, G3, G4, G5, G6, G8, G9, G10, G11 and G12, even more especially all, independently are H. In these embodiments, phosphors like depicted in FIG. 3c (2441A or 2442A) can be obtained. As indicated above, optionally, one or more, especially only one of G1, G3, G4, G5, G6, G8, G9, G10, G11, G12, D, E, I, L and M may include a covalent link with a matrix.

Hence, especially independently one or more of G2 and G7 for the organic phosphor IA (and optionally organic phosphor IB) comprise R1 or OR1, with R1 being defined by formula II. For instance, the organic phosphor IA (and optionally organic phosphor IB) may have G2 being OR1 (and e.g. G7 being H) or the organic phosphor IA (and optionally organic phosphor IB) may have G2 being R1 and G7 being OR1. Especially, G2=G7, and G2 and G7 comprise R1 or OR1, with R1 being defined by formula II. As indicated above, especially D, E, I, L and M are H.

In yet a further embodiment, two different organic phosphors IA and IA' are applied, which are all different. In yet another embodiment, four different organic phosphors are applied, which are all different. Hence, in embodiments, especially wherein one or more of (i) G9≠G12 and (ii) G10≠G11 applies, the luminescent material comprises a combination of at least two different organic phosphors defined by formulas IA and IB, IA' and IB', or in a further embodiment at least four different organic phosphors defined by formulas IA, IB, IA' and IB', wherein in the latter embodiment IA is in molar excess to IB, especially with a molar ratio of IB/IA of ≤0.5, such as ≤0.1, and IA' is in molar excess to IB', especially with a molar ratio of IB'/IA' of ≤0.5, such as ≤0.1 (specific ratios similar as defined above), with IA and IB, IA' and IB':

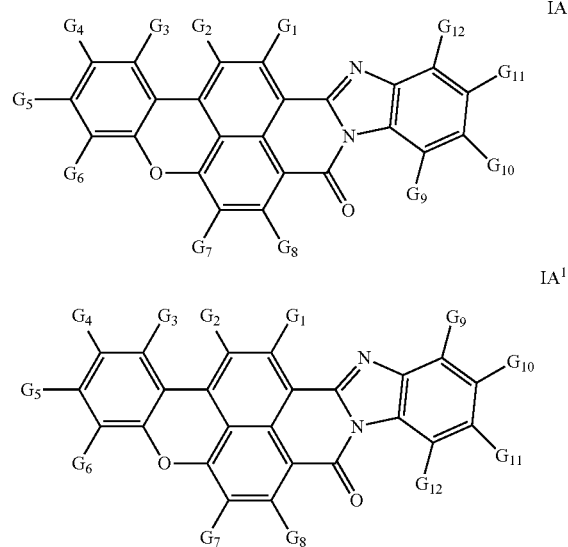

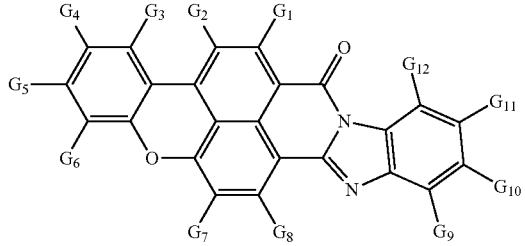

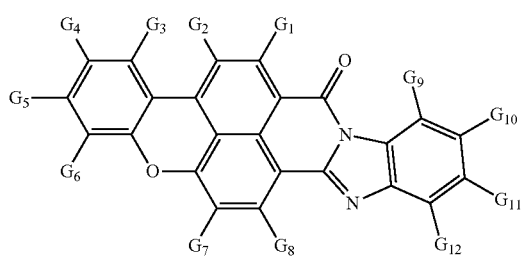

wherein G1-G12 are (for IA, IB, IA' and IB' independently) as defined above. Would G9=G12 and G10=G11, then IA=IA' and IB=IB'. Would all G1-G12 be H, then the combination of IA and IB as also shown in FIG. 3c (2410) would be obtained. Note that the combination of two different phosphors IA and IA' is a specific embodiment of phosphor IA. Note further that the combination of four different phosphors IA, IB, IA' and IB' is a specific combination of the combination of the at least two phosphors IA and IB.

It appears that such lighting device, light converter and/or luminescent material, as defined above, including the herein described specific embodiments, and as further elucidated below, may be applied efficiently and with a good life time and/or a relatively high quantum efficiency under (blue) irradiation. Relative to prior art systems, a 10-100 fold increase in life time was observed.

Herein, the term "C1-C18alkyl" may especially relate to a branched C1-C18alkyl or an unbranched C1-C18alkyl. The term "C1-C18alkyl" may relate to an unsubstituted C1-C18alkyl or substituted C1-C18alkyl (i.e. C1-C18alkyl with one or more substituents). The term "C1-C18alkyl" may relate to a linear C1-C18alkyl or non-linear C1-C18alkyl (which may be substituted or unsubstituted). The term "non-linear" herein may refer to cyclic, like C1-C18 cyclo alkyl.

By way of example, the term "C1-C18alkyl" may relate in an embodiment to a linear heptyl group, but may in another embodiment relate to a methyl substitute cyclo hexane group, with one or more fluor substituents. C1-C18alkyl especially relates to C1-C16 alkyl, like C1-C8 alkyl, such as C1-C4 alkyl.

Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, etc. Examples of cyclo alkyl groups are e.g. cyclopentyl, cyclohexyl, cycloheptyl, cyclooctyl, etc.

Optionally, the carbon chains of the C1-C18alkyl may be interrupted by one or more groups which are independently selected from —O— and —S—. Hence, in an embodiment the term C1-C18 alkyl may also relate to an ether or in a variant a polyether. Therefore, in a specific embodiment C1-C18alkyl may also refer to C1-C18alkyl comprising one or more ether groups, such as $C_nH_{2n+1}O_m$, with n being an integer from 1 to 18, such as 1-16, and with $0 \leq m \leq n/2$.

As for instance D, E, I, L and M may independently relate to OR3, C1-18alkyl may thus be part of an alkoxy group. For instance, "D" in formula II may be methoxy, etc.

Substituents that may be applied may be selected from fluorine, chlorine, hydroxyl, cyano, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, and amidino. In general, the substituents will be limited to 1-6 substituents, like 1-4 substituents. In a specific embodiment, the C1-C18alkyl is substituted with one or more fluorine atoms. For instance, in an embodiment C1-C18alkyl especially relates to $C_nH_{2+1-m}F_m$ with n being an integer from 1 to 18, such as 1-16, and with $0 \leq m \leq 2n+1$. Hence, the term "alkyl" and similar terms, may also relate to a substituted alkyl, such as an alkyl that is fluorinated with one or more fluor substituents.

Herein, the term "C6-C24aryl" may especially refer to a mono cyclic aromatic aryl group or to a polycyclic aromatic aryl group. The term "C6-C24aryl" may relate to an unsubstituted C6-C24aryl or to a substituted C6-C24aryl (i.e. C6-C24aryl with one or more substituents). C6-C24aryl especially relates to C6-C16 aryl, like C6-C10 aryl. The C6-C24aryl may in addition to at least one aryl group, also comprise one or more non-conjugated cyclic groups.

Examples of aryl groups are phenyl, naphthyl, indenyl, fluorenyl, anthracenyl, phenanthrenyl, naphthacenyl, etc. In case the C6-C24 aryl comprises one or more aromatic groups and one or more alkyl groups, like methyl phenyl (C7), or ethyl phenyl (C8), the alkyl groups may especially be linear alkyl groups. Also these alkyl groups may independently comprise one or more substituents. Further, also these alkyl groups may be interrupted by one or more groups which are independently selected from —O— and —S—. Hence, in an embodiment such alkyl group may also relate to an ether or in a variant a polyether.

Substituents that may be applied may be selected from fluorine, chlorine, hydroxyl, cyano, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, and amidino. In general, the substituents will be limited to 1-6 substituents, like 1-4 substituents. In a specific embodiment, the C6-C24aryl is substituted with one or more fluorine atoms.

Herein, the term "C6-C24 heteroaryl" may especially refer to heteroaromatic, mono- or polycyclic groups. The term "C6-C24 heteroaryl" may relate to an unsubstituted C6-C24 heteroaryl or to a substituted C6-C24 heteroaryl (i.e. C6-C24 heteroaryl with one or more substituents). C6-C24 heteroaryl especially relates to C6-C16 heteroaryl, like C6-C10 heteroaryl The C6-C24 heteroaryl may in addition to at least one heteroaryl group, also comprise one or more non-conjugated cyclic groups.

Examples of C6-C24 heteroyaryls are e.g. 2,5-indenylene, 2,6-indenylene, pyrazinylene, pyridinylene, pyrimidinylene, 2,4-thiophenylene, 2,5-thiophenylene, 1,3,4-thiadiazol-2,5-ylene, 1,3-thiazol-2,4-ylene, 1,3-thiazol-2,5-ylene, 1,3-oxazol-2,4-ylene, 1,3-oxazol-2,5-ylene, 1,3,4-oxadiazol-2,5-ylene, etc. In case the C6-C24 heteroaryl comprises one or more hetero aromatic groups and one or more alkyl groups, the alkyl groups may especially be linear alkyl groups. Also these alkyl groups may independently comprise one or more substituents. Further, also these alkyl groups may be interrupted by one or more groups which are independently selected from —O— and —S—. Hence, in an embodiment such alkyl group may also relate to an ether or in a variant a polyether.

Substituents that may be applied may especially be selected from fluorine, chlorine, hydroxyl, cyano, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, and amidino. In general, the substituents will be limited to 1-6 substituents, like 1-4 substituents. In a specific embodiment, the C6-C24 heteroaryl is substituted with one or more fluorine atoms.

In an embodiment, wherein one or more of $R_1$, $R_2$, $R_3$, $R_4$ are available, one or more of these are independently selected from the group consisting of (i) $C_nH_{2n+1}O_m$, with n being an integer from 1 to 18 and with $0 \leq m \leq n/2$, (ii) $C_nH_{2n+1-m}F_m$ with n being an integer from 1 to 18 and with $0 \leq m \leq 2n+1$, (iii) C6-C24aryl comprising one or more ether groups, (iv) C6-C24aryl comprising one or more fluor substituents, (v) C6-C24 heteroaryl comprising one or more ether groups, and (vi) C6-C24 heteroaryl comprising one or more fluor substituents.

Halogens herein are especially fluorine, chlorine, even more especially fluorine. Especially, when one or more halogens are present, the one or more halogens comprise (only) fluorine.

The phrase "independently selected from" may indicate that any of the indicated species may be chosen, independent of the other choices. For instance, in theory G1, G2, G10-G12 might be hydrogen, G3 fluorine, G4 C1-C18alkyl, G5 $OR_1$ with $R_1$ being C1-C18alkyl, G6 $NR_1R_2$, with $R_1$ being C1-C18alkyl and with $R_3$ being C6-C24aryl, G7 C6-C24 heteroaryl, G8 and G9 halogen substituted C1-C18alkyl. In general however, at least four of G1-G12 are hydrogen. Further, when one or more of $R_1$ and $R_2$ comprises a group as defined by formula II, especially at least two, more especially at least three of D,E,I,L,M are hydrogen.

In an embodiment, one or more of G1-G12 may independently also comprise an oxygen-containing alkyl group $C_nH2_{n+1}O_m$, n being an integer from 1 to 16 and $0 \leq m \leq n/2$, such as an ether or alcohol, especially an ether. Alternatively or additionally, one or more of D, E, I, L and M may independently also comprise an oxygen-containing alkyl group $C_nH2_{n+1}O_m$, n being an integer from 1 to 16 and $0 \leq m \leq n/2$. Especially, minimally two of D, E, I, L and M groups are hydrogen atoms. In yet another embodiment, G1-G12 is hydrogen.

In a specific embodiment, each of D, E, I, L and M independently comprise a group selected from hydrogen, fluorine, chlorine, isopropyl, t-butyl, methoxy, an alkyl with up to 16 carbon atoms, and an oxygen containing alkyl with up to 16 carbon atoms.

The indications above and below concerning G1-G12 in relation to organic phosphor IA may also especially apply to organic phosphor IB when available (in addition to organic phosphor IA (in the luminescent material)). Likewise, the indications herein concerning organic phosphor IA may also relate to organic phosphor IA'. Also, the indications herein concerning organic phosphor IB may also relate to organic phosphor IB'.

Further, as will be elucidated below the matrix may especially comprise an aromatic polyester, or a copolymer thereof, such as e.g. polycarbonate (PC), poly (methyl) methacrylate (P(M)MA), polyglycolide or polyglycolic acid (PGA), polylactic acid (PLA), polycaprolactone (PCL), polyethylene adipate (PEA), polyhydroxy alkanoate (PHA), polyhydroxy butyrate (PHB), poly(3-hydroxybutyrate-co-3-hydroxyvalerate) (PHBV), polyethylene terephthalate (PET), polybutylene terephthalate (PBT), polytrimethylene terephthalate (PTT), polyethylene naphthalate (PEN); especially, the matrix may comprise polyethylene terephthalate (PET). Further, as will also be elucidated below the matrix may comprise a further luminescent material embedded in the matrix. However, (PETG) (glycol modified polyethylene terephthalate), PDMS (polydimethylsiloxane), COC (cyclo olefin copolymer) PE (polyethylene), or PP (polypropylene) may also be applied as matrix. Hence, the matrix is especially a polymeric matrix.

As indicated above, organic phosphors (luminescent materials) may suffer from a relatively low photo-chemical stability. Their stability may strongly depend on the temperature of the material and on the amount of light that it converts. For this reason, organic phosphors may be suitable candidates when used in the remote configuration (see below). A lighting assembly using organic remote phosphor is relatively cheap because of the use of relatively cheap luminescent material. Furthermore, luminescent materials allow an easy design of a specific luminescent material which has a light emission spectrum anywhere in visible spectrum. Such molecules can be synthesized and depending on the molecular structure it emits a specific light.

The above described luminescent material is of the benzimidazoxanthenoisoquinolinone derivative type. Benzimidazoxanthenoisoquinolinone derivatives are known in the art and are for instance described in DE2328727.

The above described luminescent material(s) may be well excitable in the blue and/or UV.

The term "luminescent material" may especially refer to an organic material that has luminescent properties (i.e. can emit light upon excitation (by one or more of UV and blue light)). As the luminescent material of formula IA (and optionally IB) may emit especially at least in the green and/or yellow, the luminescent material is herein also indicated as green and/or yellow emitter or green and/or yellow emitting luminescent material or green and/or yellow luminescent material. However, the luminescent material of formula IA (and optionally IB) may also remit in e.g. the red.

The luminescent material may be applied in the lighting device as defined herein. Such lighting device may for instance comprise a TLED (tube with LED(s) within the tube, such as a T8 tube), which is a kind of retrofit lamp. The luminescent material may also be applied in a light bulb with LED(s) within the bulb, which is a kind of retrofit incandescent lamp. In both cases, the luminescent material may be applied remote, such as on the upstream face of the transmissive envelope (i.e. the inner face of the transmissive envelope.

Optionally, the matrix may be used as transmissive envelope of a lighting device; in other words: the transmissive envelope substantially consists of the matrix.

The term light converter may refer to a system that is configured to convert light from a first wavelength into light of a second wavelength. Especially, UV and/or blue light (excitation wavelength) may be (at least partially) converted into visible light (of higher wavelength than the excitation wavelength). Another term for "light converter" is "wavelength converter".

The light converter may be in the form of for instance particles, flakes, a film, a plate, etc. In a specific embodiment, the term light converter may include a self-supporting layer.

Hence, in an embodiment, the light converter is selected from the group consisting of a coating, a self-supporting layer, and a plate; which light converter is thus especially solid at room temperature, especially even up to 100° C., especially even up to 150° C., more especially even up to 200° C. The light converter may be flexible or may be rigid. Further, the light converter may be flat or curved (in one or two dimensions). Further, optionally the light converter may comprise outcoupling structures at at least part of the external surface of the light converter.

The light converter may comprise one or more parts, like layers on top of each other. Such parts may comprise different luminescent materials or luminescent materials in different concentration. However, at least part of the light converter comprises the (red) luminescent material.

The matrix may especially comprise a matrix material and the above indicated materials such as the luminescent material, and optionally further luminescent material, etc. The luminescent material(s) and optionally other luminescent materials may in an embodiment especially be evenly distributed throughout the matrix. However, the light converter may also comprise two or more segments, wherein two or more segments have different compositions at least with respect to the luminescent material(s), e.g. with respect to type and/or concentration of the luminescent material(s). The combination of two (or more) phosphors in embodiments according to formulas IA and IB, or in embodiments according to formulas IA, IB, IA' and IB' will in general be available as mixtures, due to the chemical process to obtain these materials. However, optionally, also layers of different compositions of phosphors as defined herein may be applied. The term "luminescent material" herein especially refers to a mixture of the two (or more) organic phosphors according to formula IA and IB (or e.g. IA, IB, IA' and IB', etc.), but with IA (and optionally also IA') in excess to IB (and optionally also IB"), whereby even molar ratios of IB/IA (and optionally IB'/IA') equal to or smaller than 0.01 may be possible.

The luminescent material(s) (i.e. at least the luminescent material according to formula IA (and/or optionally IB), but optionally also including one or more further luminescent materials), may in an embodiment molecularly be distributed through the matrix. Alternatively or additionally, the luminescent material(s) are available as particles, optionally having a coating. In the latter embodiment, coated particles may be embedded in the matrix. The coating may especially be applied to seal such particle from $H_2O$ and/or $O_2$.

Especially, the matrix material is transmissive for light having a wavelength selected from the range of 380-750 nm. For instance, the matrix material may be transmissive for blue, and/or green, and/or red light. Especially, the matrix material is transmissive for at least the entire range of 420-680 nm. Especially, the matrix material may have a light transmission in the range of 50-100%, especially in the range of 70-100%, for light generated by the light source of the lighting unit (see also below) and having a wavelength selected from the visible wavelength range. In this way, the matrix material is transmissive for visible light from the lighting unit. The transmission or light permeability can be determined by providing light at a specific wavelength with a first intensity to the material and relating the intensity of the light at that wavelength measured after transmission through the material, to the first intensity of the light provided at that specific wavelength to the material (see also E-208 and E-406 of the CRC Handbook of Chemistry and Physics, 69th edition, 1088-1989). The light converter may be transparent or translucent, but may especially be transparent. Especially, the light converter is substantially transparent and/or does not substantially scatter light. When the light converter is transparent, light of the light source may not entirely be absorbed by the light converter. Especially when using blue light, this may be of interest, as the blue light may be used to excite the light luminescent materials and may be used to provide a blue component (in white light).

The matrix (material) may comprises one or more materials selected from the group consisting of a transmissive organic material support, such as selected from the group consisting of PE (polyethylene), PP (polypropylene), PEN (polyethylene napthalate), PC (polycarbonate), polymethylacrylate (PMA), polymethylmethacrylate (PMMA) (Plexiglas or Perspex), cellulose acetate butyrate (CAB), silicone, polyvinylchloride (PVC), polyethylene terephthalate (PET), including in an embodiment (PETG) (glycol modified polyethylene terephthalate), PDMS (polydimethylsiloxane), and COC (cyclo olefin copolymer). However, in another embodiment the matrix (material) may comprise an inorganic material. Preferred inorganic materials are selected from the group consisting of glasses, (fused) quartz, transmissive ceramic materials, and silicones. Also hybrid materials, comprising both inorganic and organic parts may be applied. Especially preferred are PMMA, PET, transparent PC, or glass as material for the matrix (material). Even more especially, the matrix comprises polyethylene terephthalate (PET) as this matrix seems to give the best optical properties compared to other matrices with the same luminescent materials(s). The luminescent material degrades (under influence of light source irradiation) slowest in PET. Herein, the term "PET" may also refer to PET-G (Polyethylene Terephthalate Glycol-modified or optional other modifications. Hence, the matrix especially comprises a (polymeric) material that is especially transmissive for at least part of light generated by the luminescent material.

The light converter may especially be made by combining the luminescent material(s) and optionally other ingredients and one or more precursors of the matrix, followed by a synthesis of the matrix. For instance, in case of polymeric matrix materials this may be done by using monomeric precursors of the polymer and polymerizing the monomeric precursors, like by step-growth polymerization, or by radical chain polymerization, etc., in the presence of the luminescent material(s) and optionally other ingredients, to provide the polymeric matrix. Another option may be using as starting material(s) molecules, especially polymers, that are curable, and curing these molecules, especially polymers, in the presence of the luminescent material(s) and optionally other ingredients, to provide the matrix. Hence, especially the matrix is a polymeric matrix. The organic phosphor defined by formula IA (and optionally IB, and optionally other phosphors) may be embedded in such material. The term "embedded" may e.g. refer to the inclusion of the material as particles but may also refer to a molecular dispersion of the organic phosphors in the (polymeric) matrix material. As indicated herein, the (polymeric) matrix is especially a solid matrix. In a specific embodiment, one or more of G1, G2, G3, G4, G5, G6, G7, G8, G9, G10, G11 and G12 may comprise a covalent link with the matrix (material) (thus especially a polymeric matrix). This may for instance be obtained by providing one or more of these groups with a curable group or a polymerizable group. This may further facilitate embedding the luminescent material in the matrix. Hence, in an embodiment, one or more of G1, G2, G3, G4, G5, G6, G7, G8, G9, G10, G11 and G12 may comprise a curable or cross-linkable group.

The matrix may be coated or enclosed by a seal or coating. The coating or seal may especially be applied to seal such matrix from $H_2O$ and/or $O_2$.

As indicated above, the light converter may especially comprise a green and/or yellow luminescent material and optionally also a red luminescent material. The light converter may comprise a plurality of luminescent materials, of which at least one comprises a luminescent material according to formula I.

The term "formula (IA)", and similar terms, may also be indicated as "chemical formula (IA)". However, the light converter may also comprise a plurality of luminescent materials according to formula IA. Hence, in an embodiment, the term "luminescent material" may relate to a combination of different luminescent material all complying with formula IA. The term "formula IA" may also refer to formula IA'; likewise, the term "formula IB" may also refer to formula IB'. In embodiments, sets of different luminescent material may be present, such as IA+AB, IA' and IB', IA and IA', etc.

Further, the light converter may especially comprise a further luminescent material (see further below). However, the light converter may also comprise a plurality of further luminescent materials. Hence, in an embodiment the light converter may comprise one or more luminescent materials according to formula IA (and optionally IB (respectively)), and optionally one or more other organic luminescent materials, and optionally one or more inorganic luminescent materials. The light converter may further comprise one or more scattering materials, and optionally other materials. Phrases like "the light converter may comprise one or more luminescent materials according to formula IA (and optionally IB)" and similar phrases, indicate that one or more luminescent materials comply with formula IA, and optionally also luminescent materials may be available that comply with formula IB.

Hence, one or more further luminescent materials may be applied. The one or more further luminescent materials may also be embedded in the light converter.

Alternatively or additionally, the one or more further luminescent materials may be available in a coating on the luminescent light converter. Alternatively or additionally, the one or more further luminescent materials may be arranged within the lighting device separate from the light converter. Especially, the one or more further luminescent materials comprise a red emitting phosphor. The term "further luminescent material" especially refers to an inorganic material that has luminescent properties (i.e. can emit light upon excitation (by one or more of UV and blue light)). The further luminescent material may especially be configured to emit at least in the red, though other wavelengths are not excluded, like (also) in the yellow, green, etc. The term "further luminescent material" especially refers to an inorganic material that has luminescent properties (i.e. can emit light upon excitation (by one or more of UV and blue light)). However, the further luminescent material may in other embodiments comprise an organic luminescent material (different from the organic luminescent material(s) according to formula IA (or optionally IB)).

Hence, the further luminescent material as indicated above may especially be configured to provide red light (and optionally other light). Hence, the further luminescent material may especially be configured to convert at least part of the light of the light source into at least red light. The further luminescent material, and especially a further luminescent material (configured to provide red light), may be comprised by the light converter, especially the matrix, but may also be outside the light converter, such as a coating on the light converter.

The further luminescent material may comprise quantum dots (QDs). Amongst other narrow band emitters quantum dots are highly suitable for this purpose. Quantum dots are small crystals of semiconducting material generally having a width or diameter of only a few nanometers. When excited by incident light, a quantum dot emits light of a color determined by the size and material of the crystal. Light of a particular color can therefore be produced by adapting the size of the dots. This means that by using quantum dots any spectrum can be obtained as they are narrow band emitters.

Most known quantum dots with emission in the visible range are based on cadmium selenide (CdSe) with shell such as cadmium sulfide (CdS) and zinc sulfide (ZnS). Cadmium free quantum dots such as indium phosphide (InP), and copper indium sulfide ($CuInS_2$) and/or silver indium sulfide ($AgInS_2$) can also be used. Quantum dots show very narrow emission band and thus they show saturated colors. Furthermore, the emission color can easily be tuned by adapting the size of the quantum dots.

The quantum dots or luminescent nanoparticles, which are herein indicated as light converter nanoparticles, may for instance comprise group II-VI compound semiconductor quantum dots selected from the group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe and HgZnSTe. In another embodiment, the luminescent nanoparticles may for instance be group III-V compound semiconductor quantum dots selected from the group consisting of GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs. In yet a further embodiment, the luminescent nanoparticles may for instance be I-III-VI2 chalcopyrite-type semiconductor quantum dots selected from the group consisting of $CuInS_2$, $CuInSe_2$, $CuGaS_2$, $CuGaSe_2$, $AgInS_2$, $AgInSe_2$, $AgGaS_2$, and $AgGaSe_2$. In yet a further embodiment, the luminescent nanoparticles may for instance be I-V-VI2 semiconductor quantum dots, such as selected from the group consisting of $LiAsSe_2$, $NaAsSe_2$ and $KAsSe_2$. In yet a further embodiment, the luminescent nanoparticles may for instance be a group IV-VI compound semiconductor nano crystals such as SbTe. In a specific embodiment, the luminescent nanoparticles are selected from the group consisting of InP, $CuInS_2$, $CuInSe_2$, CdTe, CdSe, CdSeTe, $AgInS_2$ and $AgInSe_2$. In yet a further embodiment, the luminescent nanoparticles may for instance be one of the group II-VI, III-V, I-III-V and IV-VI compound semiconductor nano crystals selected from the materials described above with inside dopants such as ZnSe:Mn, ZnS:Mn. The dopant elements could be selected from Mn, Ag, Zn, Eu, S, P, Cu, Ce, Tb, Au, Pb, Tb, Sb, Sn and Tl. Herein, the luminescent nanoparticles based luminescent material may also comprise different types of QDs, such as CdSe and ZnSe:Mn.

It appears to be especially advantageous to use II-VI quantum dots. Hence, in an embodiment the semiconductor based luminescent quantum dots comprise II-VI quantum dots, especially selected from the group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe and HgZnSTe, even more especially selected from the group consisting of CdS, CdSe, CdSe/CdS and CdSe/CdS/ZnS.

In an embodiment, Cd-free QDs are applied. In a specific embodiment, the light converter nano-particles comprise III-V QDs, more specifically an InP based quantum dots, such as a core-shell InP—ZnS QDs. Note that the terms "InP quantum dot" or "InP based quantum dot" and similar terms may relate to "bare" InP QDs, but also to core-shell InP QDs, with a shell on the InP core, such as a core-shell InP—ZnS QDs, like a InP—ZnS QDs dot-in-rod.

Typical dots are made of binary alloys such as cadmium selenide, cadmium sulfide, indium arsenide, and indium phosphide. However, dots may also be made from ternary alloys such as cadmium selenide sulfide. These quantum dots can contain as few as 100 to 100,000 atoms within the quantum dot volume, with a diameter of 10 to 50 atoms. This corresponds to about 2 to 10 nanometers. For instance, spherical particles such as CdSe, InP, or $CuInSe_2$, with a diameter of about 3 nm may be provided. The luminescent nanoparticles (without coating) may have the shape of spherical, cube, rods, wires, disk, multi-pods, etc., with the size in one dimension of less than 10 nm. For instance, nanorods of CdSe with the length of 20 nm and a diameter of 4 nm may be provided. Hence, in an embodiment the semiconductor based luminescent quantum dots comprise core-shell quantum dots. In yet another embodiment, the semiconductor based luminescent quantum dots comprise dots-in-rods nanoparticles. A combination of different types of particles may also be applied. For instance, core-shell particles and dots-in-rods may be applied and/or combinations of two or more of the afore-mentioned nano particles may be applied, such as CdS and CdSe. Here, the term "different types" may relate to different geometries as well as to different types of semiconductor luminescent material. Hence, a combination of two or more of (the above indicated) quantum dots or luminescent nano-particles may also be applied.

One example, such as derived from WO 2011/031871, of a method of manufacturing a semiconductor nanocrystal is a colloidal growth process.

In an embodiment, nanoparticles can comprise semiconductor nanocrystals including a core comprising a first semiconductor material and a shell comprising a second semiconductor material, wherein the shell is disposed over at least a portion of a surface of the core. A semiconductor nanocrystal including a core and shell is also referred to as a "core/shell" semiconductor nanocrystal.

For example, the semiconductor nanocrystal can include a core having the formula MX, where M can be cadmium, zinc, magnesium, mercury, aluminum, gallium, indium, thallium, or mixtures thereof, and X can be oxygen, sulfur, selenium, tellurium, nitrogen, phosphorus, arsenic, antimony, or mixtures thereof. Examples of materials suitable for use as semiconductor nanocrystal cores include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing, including ternary and quaternary mixtures or alloys.

The shell can be a semiconductor material having a composition that is the same as or different from the composition of the core. The shell comprises an overcoat of a semiconductor material on a surface of the core semiconductor nanocrystal can include a Group IV element, a Group II-VI compound, a Group II-V compound, a Group III-VI compound, a Group III-V compound, a Group IV-VI compound, a Group I-III-VI compound, a Group II-IV-VI compound, a Group II-IV-V compound, alloys including any of the foregoing, and/or mixtures including any of the foregoing, including ternary and quaternary mixtures or alloys. Examples include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing. For example, ZnS, ZnSe or CdS overcoatings can be grown on CdSe or CdTe semiconductor nanocrystals.

Examples of semiconductor nanocrystal (core)shell materials include, without limitation: red (e.g., (CdSe)ZnS (core) shell), green (e.g., (CdZnSe)CdZnS (core)shell, etc.), and blue (e.g., (CdS)CdZnS (core)shell (see further also above for examples of specific light converter nanoparticles, based on semiconductors.

Therefore, in a specific embodiment, the light converter nanoparticles are selected from the group consisting of core-shell nano particles, with the cores and shells comprising one or more of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe, HgZnSTe, GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs.

In general, the cores and shells comprise the same class of material, but essentially consist of different materials, like a ZnS shell surrounding a CdSe core, etc.

Additionally or alternatively, the further luminescent material may also comprise other luminescent materials, such as one or more of selected from the group consisting of divalent europium containing nitride luminescent material or a divalent europium containing oxonitride luminescent material, such as one or more materials selected from the group consisting of $(Ba,Sr,Ca)S:Eu$, $(Mg,Sr,Ca)AlSiN_3:Eu$ and $(Ba,Sr,Ca)_2Si_5N_8:Eu$. In these compounds, europium (Eu) is substantially or only divalent, and replaces one or more of the indicated divalent cations. In general, Eu will not be present in amounts larger than 10% of the cation, especially in the range of about 0.5-10%, more especially in the range of about 0.5-5% relative to the cation(s) it replaces. The term ":Eu" or ":$Eu^{2+}$", indicates that part of the metal ions is replaced by Eu (in these examples by $Eu^{2+}$). For instance, assuming 2% Eu in $CaAlSiN_3:Eu$, the correct formula could be $(Ca_{0.98}Eu_{0.02})AlSiN_3$. Divalent europium will in general replace divalent cations, such as the above divalent alkaline earth cations, especially Ca, Sr or Ba. The material $(Ba,Sr,Ca)S:Eu$ can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Further, the material $(Ba,Sr,Ca)_2Si_5N_8:Eu$ can also be indicated as $M_2Si_5N_8:Eu$, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50-100%, especially 50-90% Ba and 50-0%, especially 50-10% Sr, such as $Ba_{1.5}Sr_{0.5}Si_5N_8:Eu$, (i.e. 75% Ba; 25% Sr). Here, Eu is introduced and replaces at least part of M i.e. one or more of Ba, Sr, and Ca). Likewise, the material $(Ba,Sr,Ca)AlSiN_3:Eu$ can also be indicated as $MAlSiN_3:Eu$ wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Especially, in an embodiment the further luminescent material comprises $(Ca,Sr,Mg)AlSiN_3:Eu$, preferably $CaAlSiN_3:Eu$. Further, in another embodiment, which may be combined with the former, the further luminescent material comprises $(Ca,Sr,Ba)_2Si_5N_8:Eu$, preferably $(Sr,Ba)_2Si_5N_8:Eu$. The terms "(Ca,Sr,Ba)" indicate that the corresponding cation may be occupied by calcium, strontium or barium. It also indicates that in such material corresponding cation sites may be occupied with cations selected from the group consisting of calcium, strontium and barium. Thus, the material may for instance comprise calcium and strontium, or only strontium, etc.

The further luminescent material may also comprise one or more luminescent materials selected from the group consisting of a trivalent cerium containing garnet (see above) and a trivalent cerium containing oxonitride. The oxonitride materials are in the art often also indicated as oxonitride materials.

Hence, in an embodiment the further luminescent material is configured to provide at least red light, the (organic) luminescent material comprising the two (or more) organic phosphors as defined herein is configured to provide at least green and/or yellow light, and especially the light source is configured to provide blue light. As indicated the further luminescent material comprises a quantum dot based luminescent material.

Hence, in an embodiment the light source is configured to provide blue light, the lighting device further comprises a further luminescent material configured to provide red light, wherein the further luminescent material comprises a luminescent material selected from the group consisting of $(Ba,Sr,Ca)S:Eu$, $(Mg,Sr,Ca)AlSiN_3:Eu$ and $(Ba,Sr,Ca)_2Si_5N_8:Eu$ (and optionally a quantum dot based luminescent material (see also above)) (and optionally an organic red luminescent (see also below)). Alternatively or additionally, the further luminescent material comprises a quantum dot based luminescent material. The further luminescent material may be embedded in the matrix and/or may be applied as coating to the matrix. Additionally or alternatively, the further luminescent material may also be arranged elsewhere in the lighting device, but may still be configured to convert at least part of the light source light into visible light, that may optionally complement the light of the organic luminescent material. Hence, in a specific embodiment the lighting device further comprises a quantum dot based luminescent material embedded in the matrix.

The term "further luminescent material" may thus also relate to a plurality of different further luminescent materials. The further luminescent material may be comprised by the light converter, such as embedded in the matrix, like especially the organic luminescent material, or may be outside the light converter, such as a layer on the light converter, or may be elsewhere in the lighting device. Combinations of two or more of such configurations are also possible. Hence, in an embodiment the further luminescent material, such as the quantum dot based luminescent material, is embedded in the matrix.

As indicated above, the lighting device comprises (a) a light source configured to generate light source light, and (b) a light converter configured to convert at least part of the light source light into visible converter light.

The light converter, or especially the luminescent material, is configured to convert at least part of the light source light. In order words, one may say that the light source is radiationally coupled to the light converter, especially the luminescent material. When the light source comprises a substantially UV light emitting light source, the luminescent material may be configured to convert substantially all light source light that impinges on the luminescent material. In case the light source is configure to generate blue light, the luminescent material may partly convert the light source light. Dependent upon the configuration, a part of the remaining light source light may be transmitted through a layer comprising the luminescent material. Here, the term may relate to one or more of the organic luminescent material and the further luminescent material.

The term light source may in principle relate to any light source known in the art, but may especially refers to a LED-based light source, herein further indicated as LED. The description below will—for the sake of understanding—only addresses LED-based light sources. The light source is configured to provide UV and/or blue light. In a preferred embodiment, the light emitting diode is configured to generate LED light with a blue component. In other words, the light source comprises a blue LED. Hence, in an embodiment, the light source is configured to generate blue light. Especially, the LED is a solid state LED. The term "light source" especially relates to an electrical light source, such as a solid state light source, like a LED or solid state laser.

In yet another embodiment, the light emitting diode is configured to generate LED light with a UV component. In other words, the light source comprises a UV LED. When a UV light source is applied and blue or white light is desired, as blue component, for instance the well-known materials $BaMgAl_{10}O_{17}:Eu^{2+}$ and/or $(Sr,Ba,Ca)_5(PO_4)_3Cl:Eu^{2+}$ may be applied. However, also other luminescent materials that are able to convert UV light into blue light may alternatively or additionally be applied. Such blue luminescent material may be applied as part of the light source, or remote, and may optionally (also) be comprised by the light converter. All luminescent materials described herein may be radiationally coupled with the light source, though optionally one or more luminescent materials are radiationally coupled with one or more other luminescent materials (i.e. they are configured to receive mission light of those one or more other luminescent materials, and can get be excited by that emission light).

Preferably, the light source is a light source that during operation emits at least light at a wavelength selected from the range of 200-490 nm, especially a light source that during operation emits at least light at wavelength selected from the range of 400-490 nm, even more especially in the range of 440-490 nm. This light may partially be used by the luminescent material(s) (see below). In a specific embodiment, the light source comprises a solid state LED light source (such as a LED or laser diode). The term "light source" may also relate to a plurality of light sources, such as 2-20 (solid state) LED light sources. Hence, the term LED may also refer to a plurality of LEDs. Hence, in a specific embodiment, the light source is configured to generate blue light. In a further embodiment, the lighting device might be applied as back lighting unit in an LCD application. Hence, the invention provides in a further aspect a liquid crystal display device comprising a back lighting unit, wherein the back lighting unit comprises one or more lighting devices as defined herein.

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL.

In an embodiment, the light source may also provide light source light having a correlated color temperature (CCT) between about 5000 and 20000 K, e.g. direct phosphor converted LEDs (blue light emitting diode with thin layer of phosphor for e.g. obtaining of 10000 K). Hence, in a specific embodiment the light source is configured to provide light source light with a correlated color temperature in the range of 5000-20000 K, even more especially in the range of 6000-20000 K, such as 8000-20000 K. An advantage of the relative high color temperature may be that there may be a relative high blue component in the light source light.

The lighting device comprises at least the light converter comprising the organic luminescent material according to formula IA (and optionally IB). Other (further) luminescent materials, may also be present. The one or more further luminescent materials may each individually be comprised by the matrix but may also be provides as coating or layer on the matrix, or may be arranged elsewhere in the lighting device.

The lighting device may especially be configured to be able to provide white light. Optionally, the lighting device is configured to provide colored light or is configured to be able to provide color light and white light, depending upon how the lighting device is controlled.

The terms "violet light" or "violet emission" especially relates to light having a wavelength in the range of about 380-440 nm. The terms "blue light" or "blue emission" especially relates to light having a wavelength in the range of about 440-490 nm (including some violet and cyan hues). The terms "green light" or "green emission" especially relate to light having a wavelength in the range of about 490-560 nm. The terms "yellow light" or "yellow emission" especially relate to light having a wavelength in the range of about 540-570 nm. The terms "orange light" or "orange emission" especially relate to light having a wavelength in the range of about 570-600. The terms "red light" or "red emission" especially relate to light having a wavelength in the range of about 600-750 nm. The term "pink light" or "pink emission" refers to light having a blue and a red component. The terms "visible", "visible light" or "visible emission" refer to light having a wavelength in the range of about 380-750 nm.

The light source may be configured in a chamber, with reflective wall(s) (such as coated with a reflective material like $TiO_2$), and a light transmissive window. In an embodiment, the window is the light conversion layer. In yet a further embodiment, the window comprises the light conversion layer. This layer may be arranged upstream of the window or downstream of the window. In yet a further embodiment, light conversion layers are applied at both sides of the window.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

It may be advantageous, in view of efficiency and/or stability, to arrange the light converter (and optionally also other luminescent material(s) not within the light converter), at a non-zero distance, such as 0.5-50 mm, like 1-50 mm, from the light source. Hence, in an embodiment, the light converter may be configured at a non-zero distance of the light source. For instance, the light converter, or especially the (organic) luminescent material(s), may be applied to or may be comprised by a window of the lighting unit. Hence, in an embodiment, the light converter is configured at a non-zero distance from the light source. Note however that the invention is not limited to applications wherein the distance between the light converter and the light source is non-zero. The invention, and the herein described specific embodiments, may be also applied in other embodiments wherein the light source and light converter are in physical contact. In such instances, the light converter may especially be configured in physical contact with e.g. a LED die.

In case the light source is configured to provide blue light, the luminescent material may be configured to convert only part of the light source light. In an embodiment, the blue light of the light source and the light of the organic luminescent material light and the light of the optional further luminescent material, such as a nano particles based luminescent material, together may in an embodiment provide white light.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

The phrases "aryl group containing" or "heteroaryl group containing" and similar phrases indicate that such hydrocarbon at least comprises an aryl group or a heteroaryl group, respectively, but may in embodiments also comprise two or more of such groups, respectively.

The invention provides in a further aspect one or more of the individual phosphors (i.e. one or more isomers). In an embodiment, the invention especially provides the 2410A phosphor. In an embodiment, the invention provides the 24105B phosphor. In an embodiment, the invention especially provides the 2441A phosphor. In an embodiment, the invention provides the 2441B phosphor. In an embodiment, the invention especially provides the 2442A phosphor. In an embodiment, the invention provides the 2442B phosphor. In an embodiment, the invention especially provides the 2463A phosphor. In an embodiment, the invention provides the 2463B phosphor. In an embodiment, the invention especially provides the 2475A phosphor. In an embodiment, the invention provides the 2475B phosphor. In an embodiment, the invention especially provides the 2485A phosphor. In an embodiment, the invention provides the 2485B phosphor. The invention further provides a matrix comprising a luminescent material comprising such (individual) organic phosphor. As indicated above, especially those phosphors provide desired properties when the two O-atoms in the ring are at the same side of the molecule (A-type arrangement). Yet, the invention further provides a luminescent material comprising such (individual) organic phosphor. The invention further provides a lighting device and a light converter, wherein the light converter comprises a luminescent material comprising such (individual) organic phosphor. The luminescent material and the light source are especially radiationally coupled (see also above). The invention further refers to derivatives of the herein indicated monomers. In a specific embodiment, the invention provides a luminescent material according to any one of the preceding claims 13-14, comprising an organic phosphor selected from the group consisting of 6,16-diphenyl-8H-benzo[3,4]isochromeno[7,8,1-def]benzo[4,5]imidazo[1,2-b]isoquinolin-8-one (2441A); 6,16-diphenoxy-8H-benzo[3,4]isochromeno[7,8,1-def]benzo[4,5]imidazo[1,2-b]isoquinolin-8-one (2442A); 16-phenoxy-8H-benzo[3,4]isochromeno[7,8,1-def]benzo[4,5]imidazo[1,2-b]isoquinolin-8-one (2463A); 6,16-bis(4-(2,4,4-trimethylpentan-2-yl)phenoxy)-8H-benzo[3,4]isochromeno[7,8,1-def]benzo[4,5]imidazo[1,2-b]isoquinolin-8-one (2475A); and 16-(4-(2,4,4-trimethylpentan-2-yl)

phenoxy)-8H-benzo[3,4]isochromeno[7,8,1-def]benzo[4,5]imidazo[1,2-b]isoquinolin-8-one (2485A); or such organic phosphor per se.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
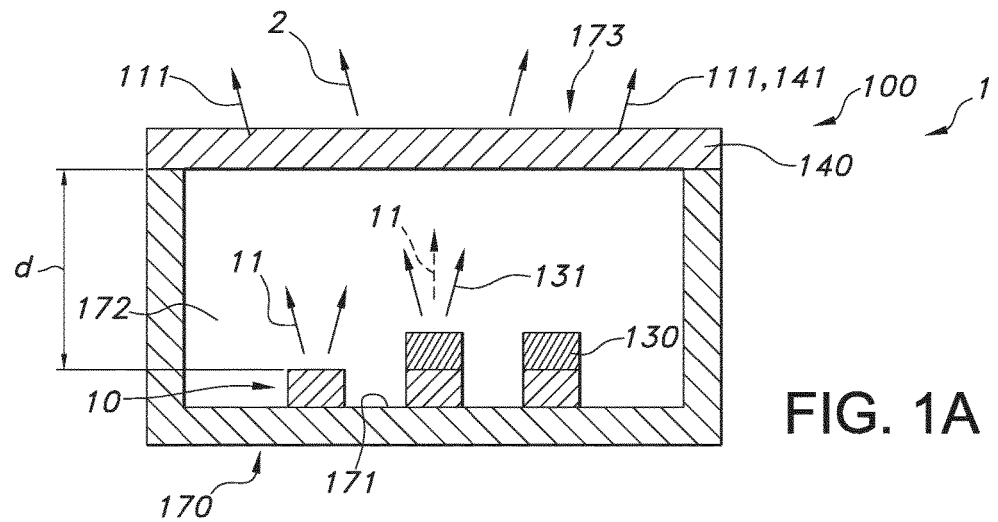
FIGS. 1a-1f schematically depict some embodiments of the lighting device; these drawings are not necessarily on scale.

FIG. 1a schematically depicts a lighting device 1 with a light converter 100, which in this embodiment at least comprises the luminescent material 140 according to formula 1. The luminescent material 140 is in this embodiment embedded in a (polymeric) matrix, such as PET. As can be seen, a remote version is shown, with a non-zero distance d between the luminescent material (in the light converter 100) and the light source(s), indicated with reference(s) 10. The lighting device 1 comprises one or more light sources 10 which are configured to provide light source light 11, especially blue and/or UV light. The lighting device 1 may comprise a plurality of such light sources. When lighting device light, indicated with reference 2, of a white nature is desired, it may be necessary to us an RGB concept, wherein the green and/or yellow color, or at least part thereof, is provided by the green and/or yellow luminescent material 140, and the blue and red light are provided by one or more of the light source and a combination of the light source and another luminescent material, especially the further luminescent material. The further luminescent material is indicated with reference 130, and provides further luminescent material light 131.

The luminescent material 140 according to formula I provides upon excitation by the light source light 11 and/or by emission of one or more other luminescent materials, such as e.g. the further luminescent material light 131, luminescent material light 141. Here, the light converter 100 is remote from the light source 10, and the luminescent material, which is embedded in the light converter 100, is thus also remote. The optional further luminescent material 130 can also be arranged remote, see below, but is by way of example close to the light source 10, such as in a dome and/or as layer on the LED die.

Just by way of example, one light source has been depicted without the further luminescent material 130. However, in another embodiment, all light sources 10 may be configured with at least further luminescent material 130. Also, by way of example three light sources 10 have been depicted. However, more or less than three light sources may be applied.

Note that the light source 10 may provide blue and/or UV light. The further luminescent material 130 may especially, upon excitation (by said light of the light source 10) provide red light. Optionally, the further luminescent material 130 may also provide green and/or yellow light.

FIG. 1a, and other figures, schematically depict a device with a light chamber 170, with an enclosure 171, at least partly enclosing a cavity 172, which has a transmissive part 173. In an embodiment, the transmissive part 173 comprises the light converter 100, or may especially consist of the light converter 100. The surface of the non-transmissive part of the enclosure is indicated with reference 171. At least part of the surface 171 may comprise a reflector, such as a reflective coating.

The light converter 100 provides upon excitation light converter light 111, which at least comprises luminescent material light 141 but may optionally comprise other luminescence light as well (see below). The lighting device light, indicated with reference 2, at least comprises light converter light 111/luminescent material light 141, but may optionally comprise one or more of the light source light 11, further luminescent material light 131, and light of other luminescent materials (not depicted).

Figure 1B:
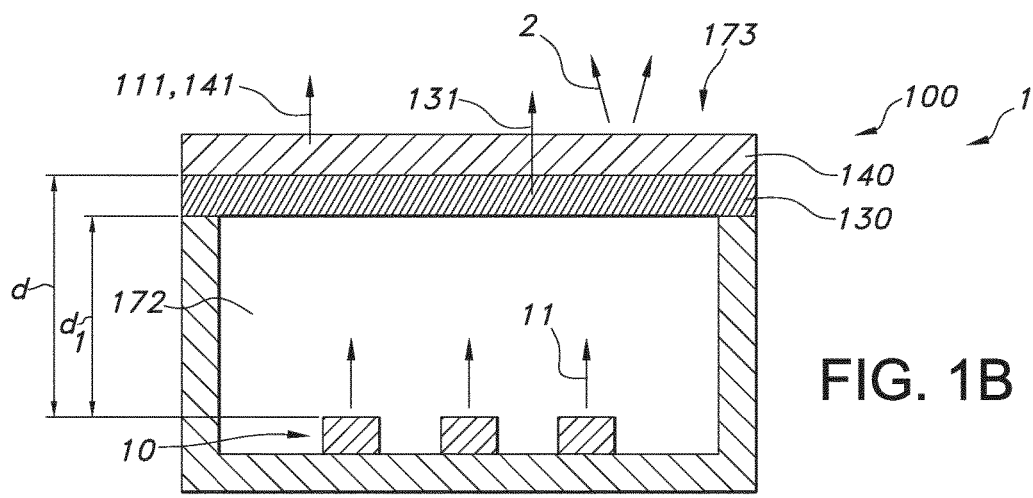

FIG. 1b schematically depicts an embodiment wherein the light converter 100 may comprise an upstream layer with further luminescent material 130. Optionally, this may be a light converter comprising two layers comprising the same matrix, but comprising different luminescent materials. The distance of the layer with further luminescent material 130 to the light source is indicated with d1. This distance is in this embodiment non-zero, in contrast to the embodiment schematically depicted in FIG. 1a.

Figure 1C:
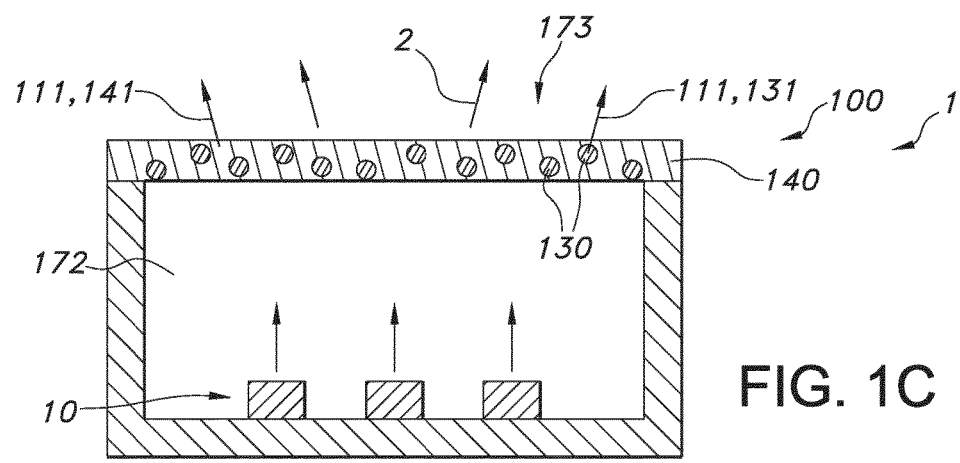

FIG. 1c schematically depicts an embodiment wherein the light converter 100 comprises the further luminescent material 140, e.g. in the form of quantum dots, and the luminescent material 130 according to formula IA. Both the luminescent material 140 and the further luminescent material 130 are in this embodiment embedded in the (remote) light converter, i.e. embedded in the (polymeric) matrix of the light converter 100.

Figure 1D:
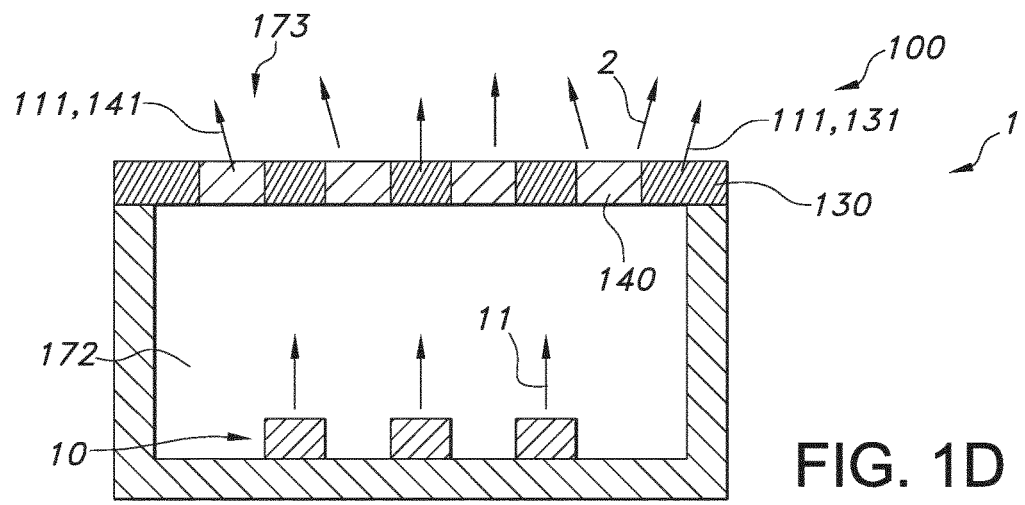

FIG. 1d schematically depicts an embodiment wherein the transmissive part 173 comprises at least two types of segments, with volumes over 0.25 cm$^3$, wherein the two types of segments comprise different weight ratios luminescent material and further luminescent material. For instance, first segments only comprise the luminescent material 140 as luminescent material and second segments only comprises further luminescent material 130 as luminescent material. The luminescent material 140 may also in this embodiment be embedded in a (polymeric) matrix, such as PET. Likewise, also the further luminescent material 130 may be embedded in a (polymeric) matrix, such as PET.

Figure 1E:
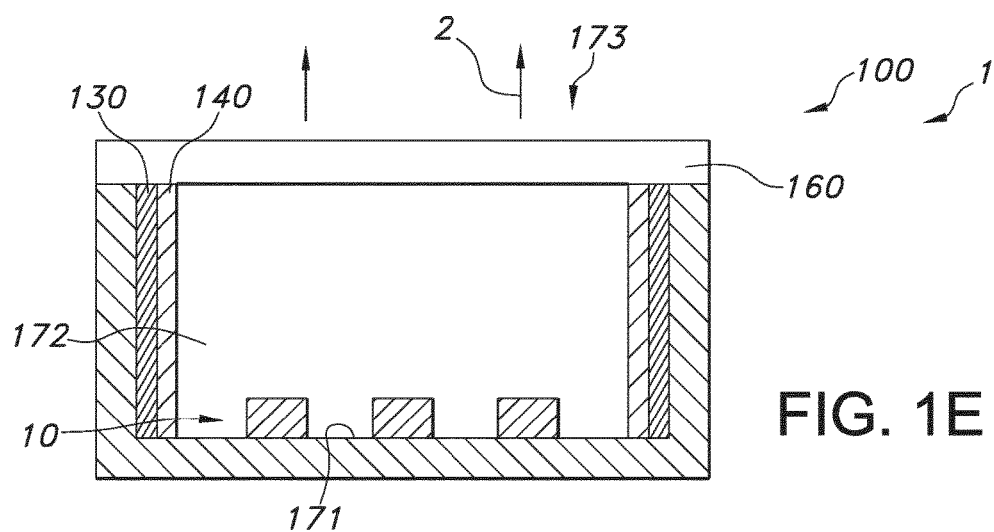

FIG. 1e schematically depicts an embodiment wherein the enclosure 170 comprises a transmissive diffuser 160 (as transmissive part 173) and the light converter is applied to at least part of the non-transmissive part of the enclosure 171.

Figure 1F:
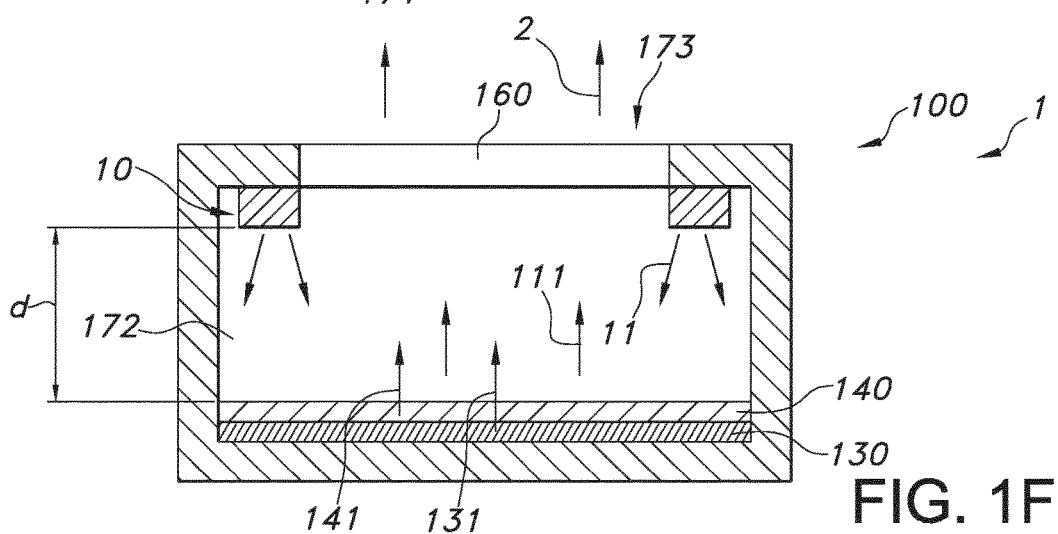

FIG. 1f schematically depicts a reflective configuration. As mentioned above, the luminescent material 140 and optionally the further luminescent material 140 may (both) be embedded in a (polymeric) matrix.

Combinations of embodiments may also be applied, like the segmented light converter of FIG. 1d in combination with or alternative to the light converter(s) shown in the other drawings, such as e.g. 1a, 1b, 1e, 1f.

In FIGS. 1a-1d, the lighting device comprises a light transmissive window, which comprises or consists of the matrix. Hence, the matrix may be applied as light transmissive window. In FIGS. 1e-1f, a transmissive diffuser is used as transmissive window. The transmissive window is used as an envelope, or as part of an envelope. Here, the transmissive window envelopes at least part of the cavity 172. Note that the transmissive window is not necessarily flat. The transmissive window, comprising in embodiments the matrix, may also be curved, like in the embodiment of a TLED or in a retrofit incandescent lamp (bulb).

Figure 2A:
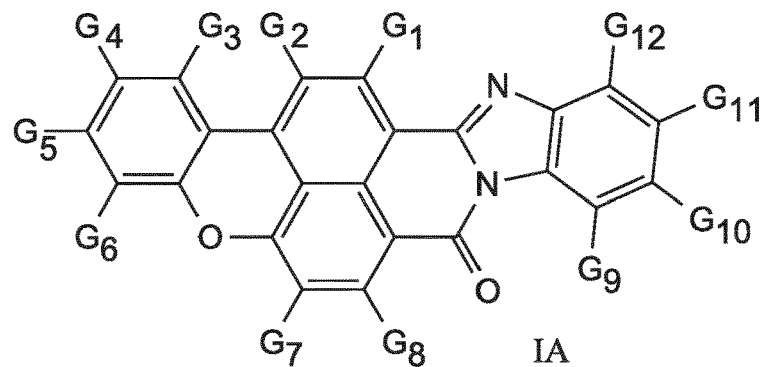
FIG. 2a-2c show some information on the phosphors according to formulas IA and IB.
Figure 2A:
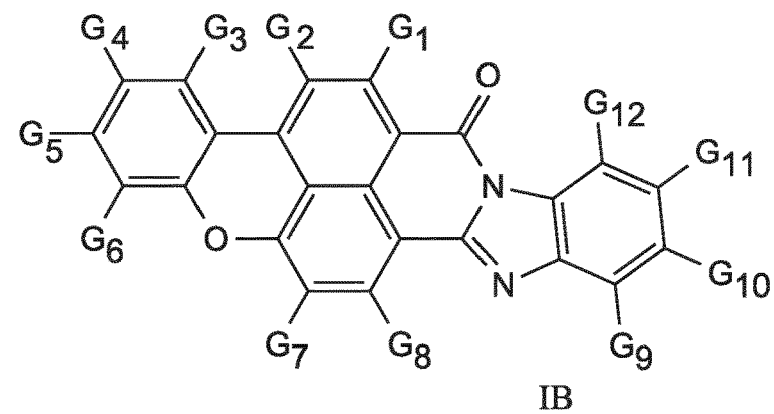
Figure 2B:
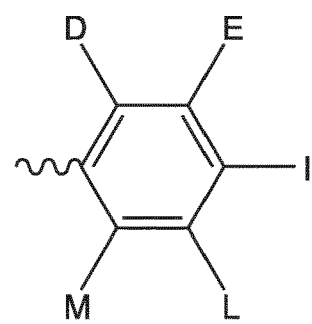
Figure 2C:
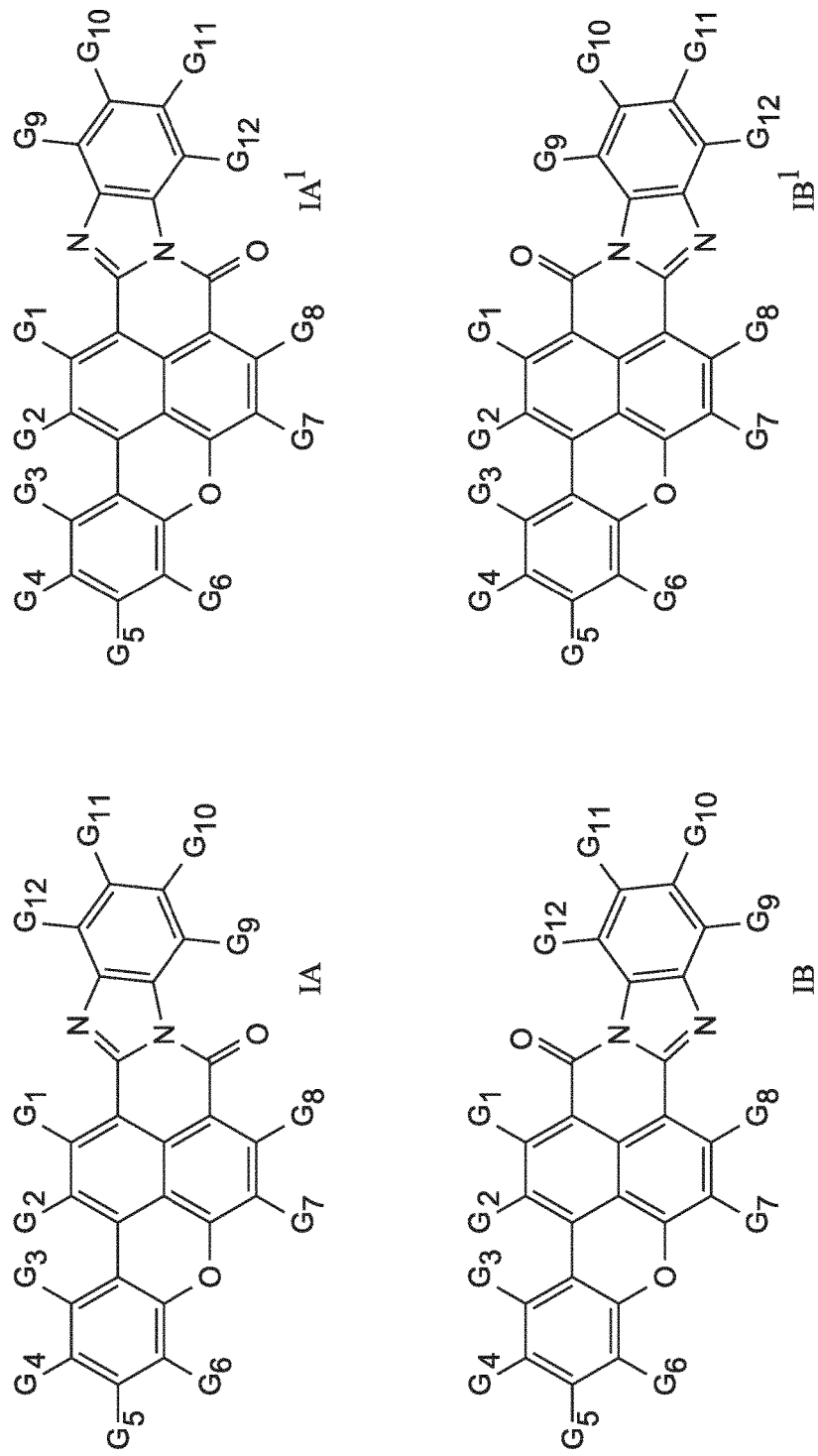

FIG. 2a shows the (combination of) phosphors according to formula IA and IB, which combination, but at least IA, may be available in the luminescent material as described above in relation to some specific device embodiments. FIG. 2b shows the group with formula II, which may be substituent or which may be part of a substituent (one or more of G1-G12 (in one or more of IA and IB)). Under specific conditions, especially when G9≠G12 and when G10≠G11, four different systems may be obtained, as indicated in FIG. 2c, with formulas IA, IA', IB, IB'. The luminescent material at least comprises one or more phosphors according to one or more of formula IA and IA', and optionally one or more phosphors according to one or more of formula IB and IB", and optionally one or more other (organic and/or inorganic) phosphors.

EXAMPLES

Figure 3A:
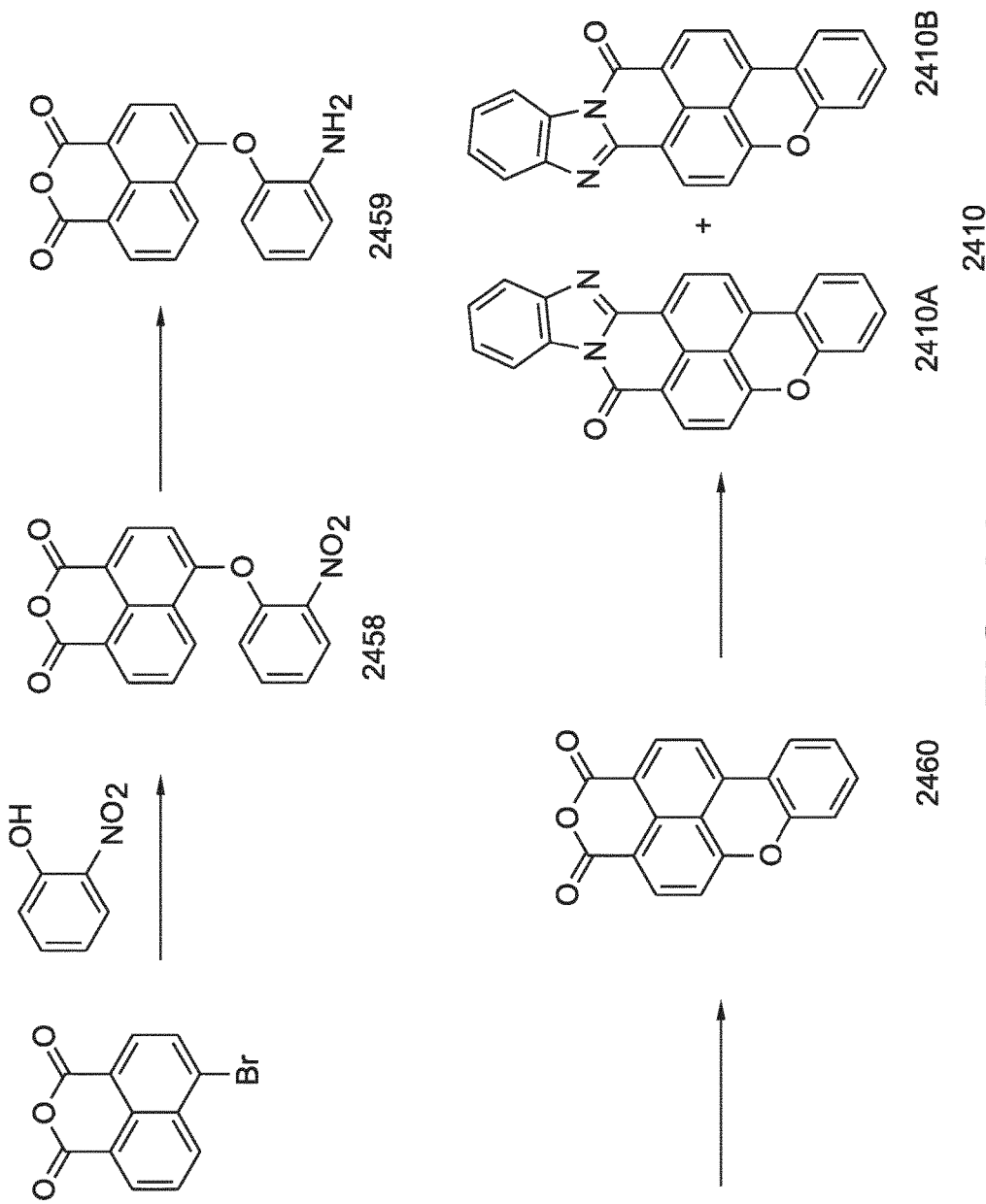
FIGS. 3a-3c show a synthesis scheme and a number of luminescent materials made, respectively.
Figure 3B:
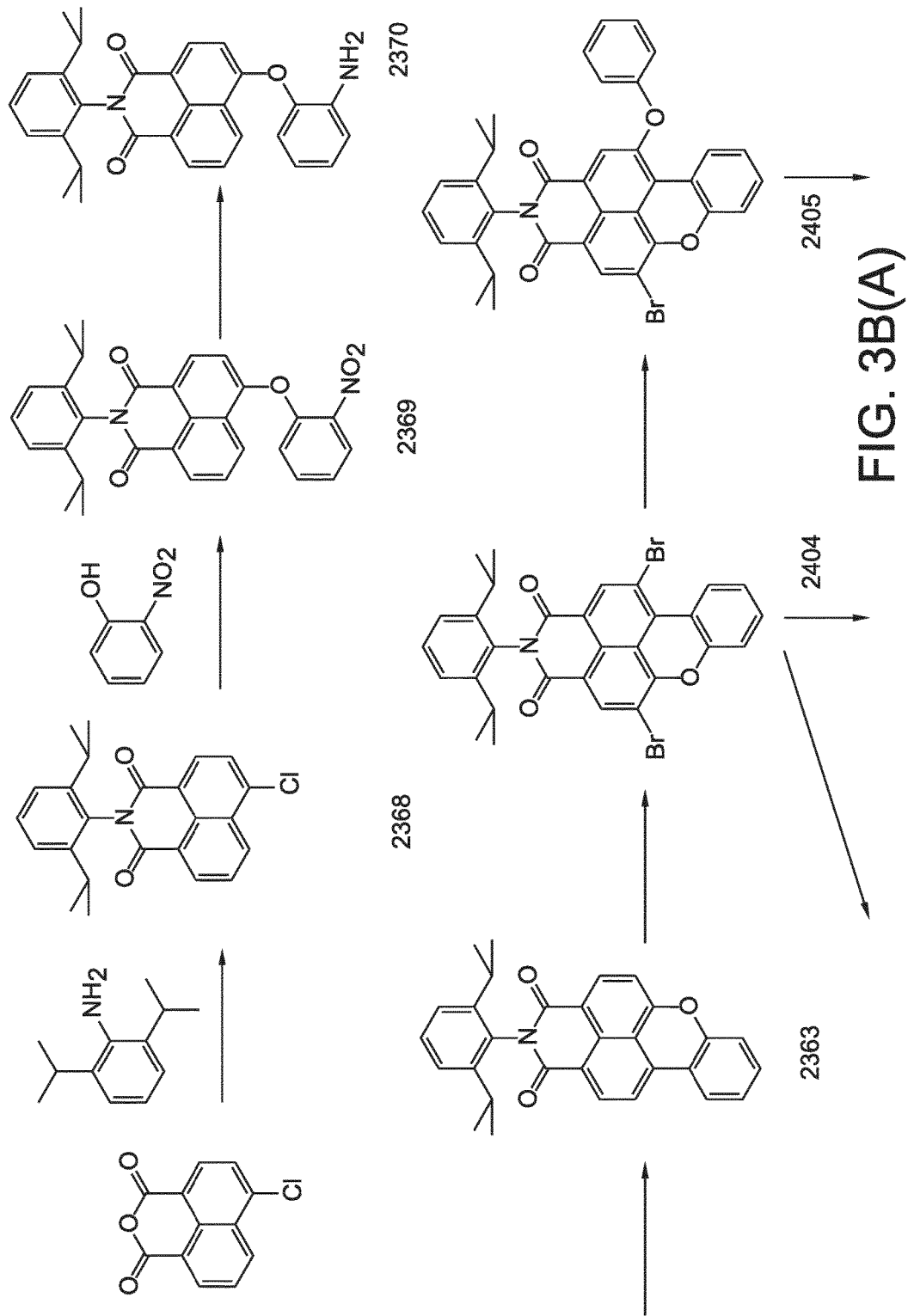
Figure 3B:
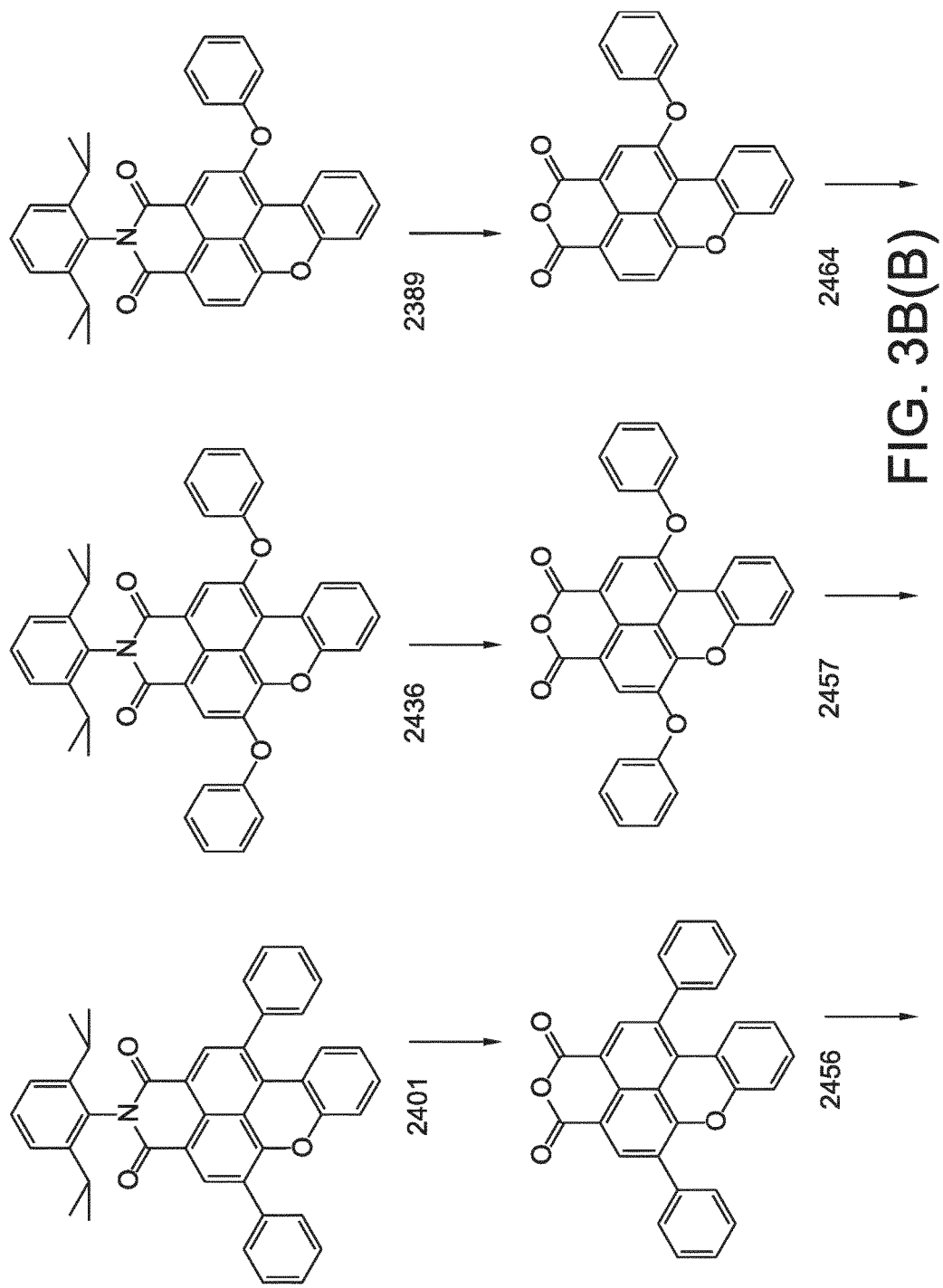
Figure 3B:
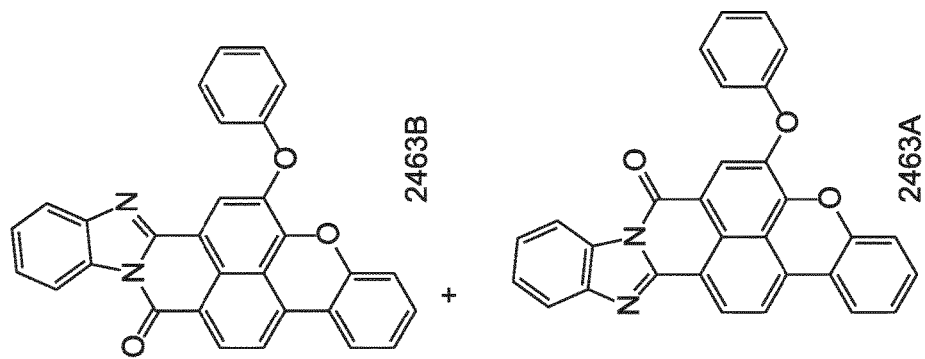
Figure 3B:
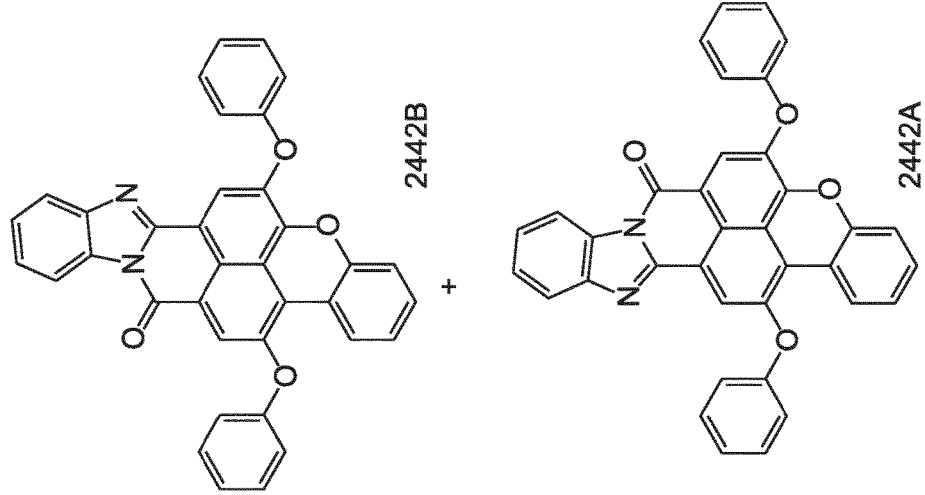
Figure 3B:
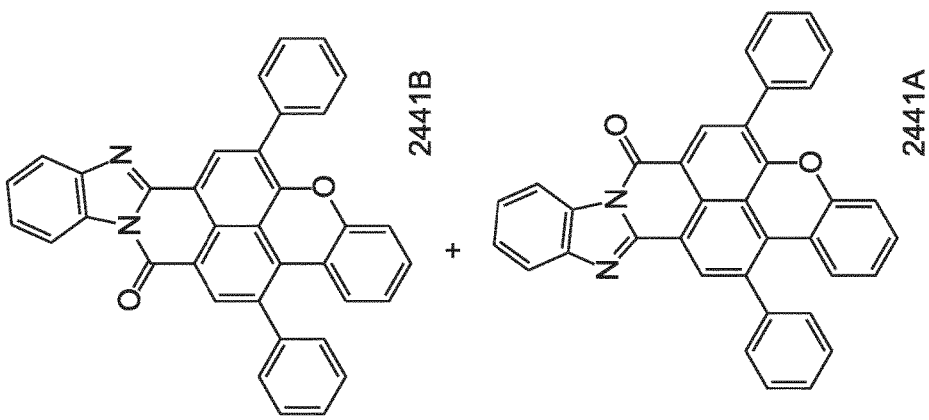
Figure 3C:
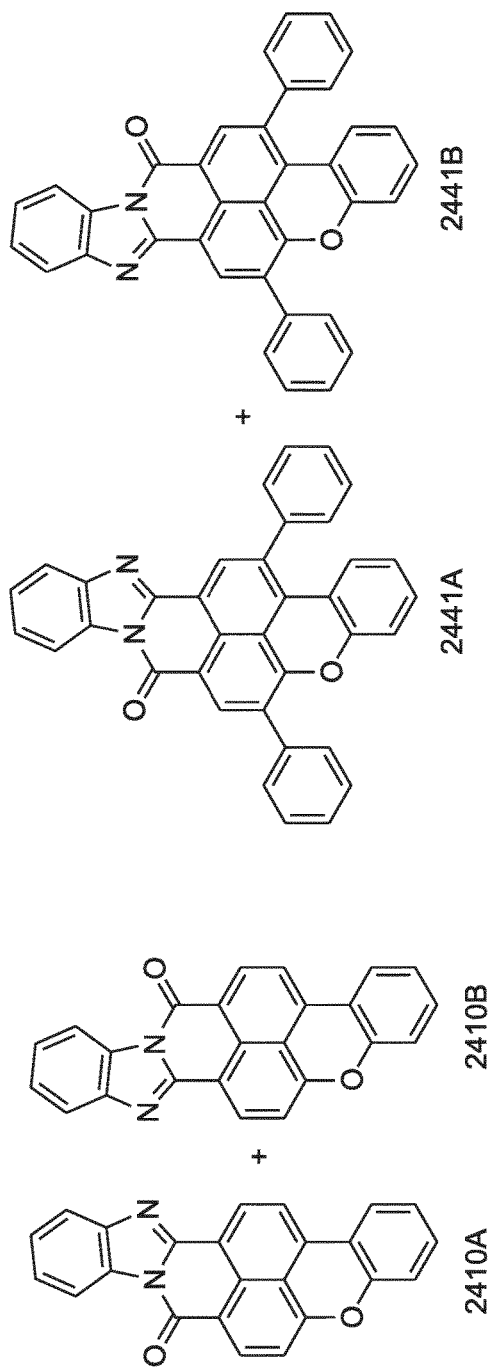
Figure 3C:
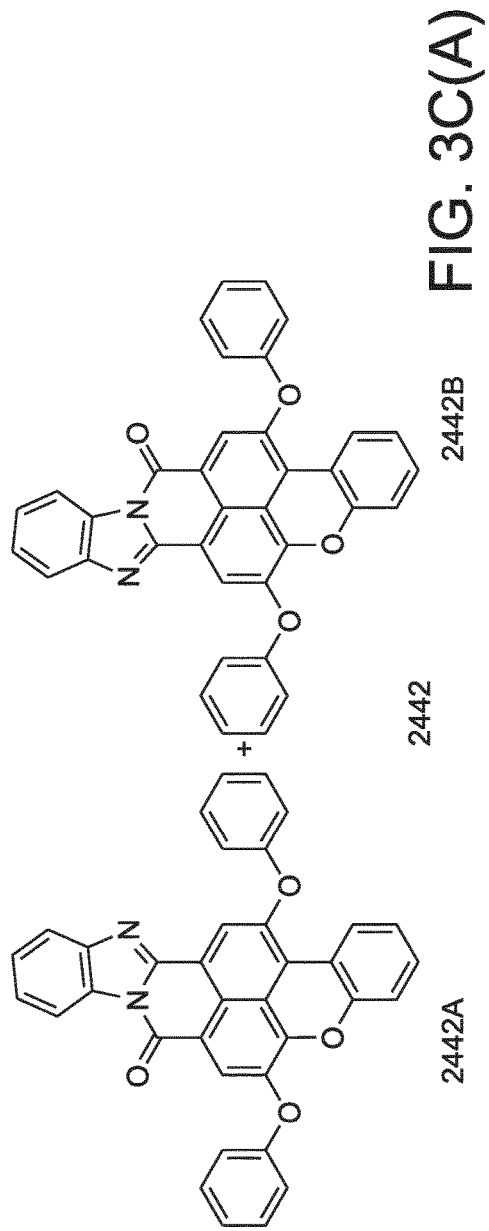
Figure 3C:
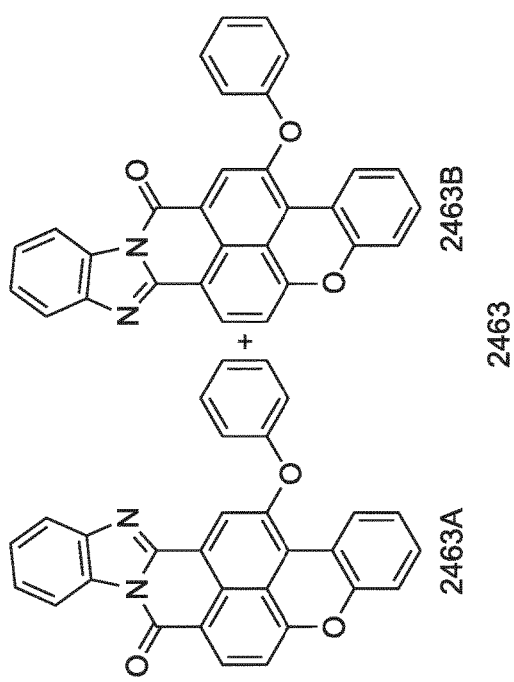
Figure 4A:
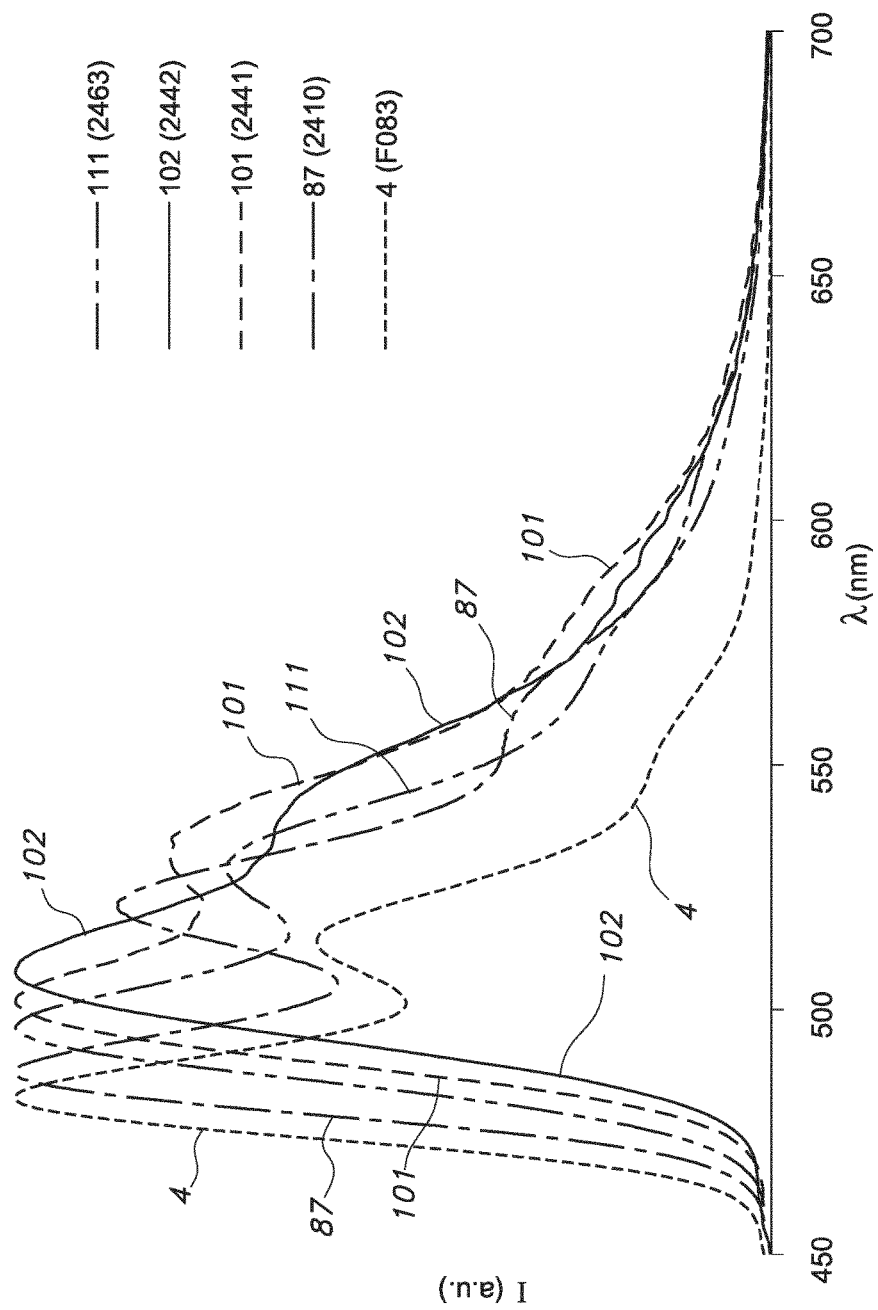
FIG. 4a shows luminescence spectra (at RT) in ethyl acetate of those materials, also in comparison with F083 (state of the art perylene derivative)

By way of example, a few syntheses are described below. A synthesis scheme is depicted in FIGS. 3a-3c. Luminescence spectra of those materials, also in comparison with F083 (prior art system), are depicted in FIG. 4a.

Synthesis of 2410 (Mixture of Isomers):

1. 4-(2-nitrophenoxy)-1,8-naphthalic Anhydride 2458

A mixture of 4-bromonaphthalic anhydride (50 g, 180.46 mmol), 2-nitrophenol (50.2 g, 360.92 mmol) and NaOH (13 g, 325.17 mmol) and copper powder (1.9 g) in DMF (1 L) was refluxed for 2 h under nitrogen. The mixture was cooled and poured into aqueous hydrochloric acid (20%, 1 L) and the precipitated solid was filtered, washed with water and recrystallized in AcOH to afford a mixture of starting material and expected compound 2458. Washing of the solid with hot toluene removed the unreacted starting material and afforded after drying under vacuum compound 2458 (11.5 g, 10%) as a beige solid.

2. 4-(2-aminophenoxy)-1,8-naphthalic Anhydride 2459

A suspension of compound 2458 (11.0 g, 32.81 mmol) in 1,4-dioxane (800 mL) under nitrogen atmosphere was warmed to get a clear solution. The mixture was then cooled to 60° C. and 10% Pd/C (2.5 g) was added. The mixture was stirred 20 h at 60° C. under hydrogen atmosphere (balloon) then cooled to 40° C. filtered over a pad of celite and concentrated to give crude compound 2459 (9.5 g, 95%) as a yellow solid used as such in the next step.

3. Benzo[k,l]xanthene-3,4-dicarboxylic Anhydride 2460

A solution of compound 2459 (6.1 g, 19.98 mmol) in AcOH (120 mL) was treated with concentrated hydrochloric acid (5.3 mL) and water (7 mL) at 0-5° C. A solution of sodium nitrite (1.6 g, 23.98 mmol) in water (10 mL) was added drop wise and the mixture was stirred at 0-8° C. for 2 h. The diazonium solution was added portion wise to a boiling solution of hydrated copper(II) sulphate (13.4 g, 53.75 mmol) in water (180 mL) and acetic acid (11 mL) over 30 minutes. After the addition was complete, the mixture was boiled for a further 30 minutes, cooled and filtered. The precipitate obtained was washed with water and recrystallized from DMF to afford the title compound (1.2 g, 21%) as a yellow solid.

4. Mixture of 8H-benzo[3,4]isochromeno[7,8,1-def] benzo[4,5]imidazo[1,2-b]isoquinolin-8-one and 7H-benzo[3,4]isochromeno[7,8,1-def]benzo[4,5] imidazo[2,1-a]isoquinolin-7-one: 2410

A mixture of 1460 (260 mg, 0.90 mmol) and o-phenylenediamine (215 mg, 1.98 mmol) in propionic acid (30 mL) and was stirred for 20 h at 140° C. The yellow solution became red. The mixture was cooled to room temperature and poured into 5% aqueous hydrochloric acid (30 mL) and the precipitate was collected by filtration, washed with water and recrystallized from DMF. The crystals obtained were washed with methanol and dried to afford the title compounds (mixture of isomers, 270 mg, 83%) as an orange solid poorly soluble at room temperature. $\lambda$(exc) (ethyl acetate)=447 nm and 475 nm. $\lambda$(em) (ethyl acetate) 487 nm and 521 nm. The term "$\lambda$(exc)" indicates the excitation wavelength (i.e. the wavelength at which is excited); the term "$\lambda$(em)" indicates the emission wavelength (i.e. the emission wavelength at which the emission is monitored).

See also FIGS. 3a, 3c (2410) and 4a (87(2410)).

Synthesis of 2441 (Mixture of Isomers):

1. 6-chloro-2-(2,6-diisopropylphenyl)-1H-benzo[de] isoquinoline-1,3(2H)-dione (2368)

A mixture of 4-chloronaphthalic anhydride (10 g, 43.0 mmol) and 2,6-diisopropylaniline (16.2 mL, 86 mmol) in AcOH (300 mL) was refluxed overnight. The mixture was cooled and poured into water. The precipitate was collected by filtration, washed with water and dried under vacuum. Purification by column chromatography on $SiO_2$ (DCM/heptane=2:1) gave 7.5 g (44%) of pure compound 2368.

2. 4-(2-nitrophenoxy)-N-(2,6-diisopropylphenyl)-1, 8-naphthalimide (2369)

A mixture of 2368 (7.5 g, 19.1 mmol), 2-nitrophenol (13.5 g, 34.4 mmol) and $K_2CO_3$ (5.3 g, 38.2 mmol) in NMP (300 mL) was stirred at 90° C. under nitrogen overnight. The mixture was cooled and poured into a mixture of AcOH (150 mL) and ice-water. After 5 minutes, 2 N HCl (200 mL) was added and the mixture was extracted with toluene (4×). The combined organic layers were washed with water and brine, dried ($Na_2SO_4$), filtered and concentrated. Purification by column chromatography on SiO$_2$ (DCM/heptane=1/1 to 2:1) gave 6.7 g (71%) of pure compound 2369 as a white solid.

3. 4-(2-aminophenoxy)-N-(2,6-diisopropylphenyl)-1,8-naphthalimide (2370)

A solution of compound 2369 (5.7 g, 11.5 mmol) in a mixture of THF (60 mL) and MeOH (50 mL) under nitrogen atmosphere was warmed to get a clear solution. The mixture was then cooled to room temperature and 10% Pd/C (2 g) was added. The mixture was stirred 2 h at room temperature under hydrogen atmosphere (balloon) then filtered over a pad of celite and concentrated. Purification by column chromatography on SiO$_2$ (DCM) gave 4.9 g (90%) of pure compound 2370 as a yellow solid.

4. 2-(2,6-diisopropylphenyl)-1H-xantheno[2,1,9-def]isoquinoline-1,3(2H)-dione (2363)

A solution of compound 2370 (5.1 g, 11.0 mmol) in AcOH (80 mL) was treated with hydrochloric acid (1.5 M, 21 mL) and sodium nitrite (3.0 g, 43.9 mmol in 20 mL water) at 0° C. After 60 minutes, a solution of CuSO$_4$.5H$_2$O (11.24 g, 45.0 mmol) in water (130 mL) was added. The mixture was refluxed for another 0.5 h and then allowed to cool. The precipitated yellow solid was filtered, washed with water and dried under vacuum. Purification by column chromatography on SiO$_2$ (DCM/heptane=1/1 to 2:1) gave 850 mg (17%) of pure compound 2363 as a yellow solid. M+H=448.1. $\lambda_{max}$ (ethyl acetate)=421 nm, ε=25500 and 444 nm ε=21300. λ(em) (ethyl acetate) 460 nm and 490 nm.

5. 5,11-dibromo-2-(2,6-diisopropylphenyl)-1H-xantheno[2,1,9-def]isoquinoline-1,3(2H)-dione (2404)

Bromine (2.7 mL, 53.64 mmol) was added to a solution compound 2363 (2 g, 4.47 mmol) in CHCl$_3$ (160 mL) under nitrogen. The mixture was stirred at 60° C. for 5 h cooled to room temperature and concentrated. The various brominates products were separated by column chromatography (SiO$_2$, eluent: toluene/DCM 1/1 to 2/1). Compound 2404 (1.8 g, 66%) was obtained as a yellow solid.

6. 2-(2,6-diisopropylphenyl)-5,11-diphenyl-1H-xantheno[2,1,9-def]isoquinoline-1,3(2H)-dione (2401)

Compound 2404 (500 mg, 0.83 mmol), phenylboronic acid (810 mg, 6.64 mmol), Pd(PPh$_3$)$_4$ (40 mg, 0.03 mmol) and Na$_2$CO$_3$ (265 mg, 2.50 mmol) were added to a degassed mixture of EtOH (1 mL), benzene (15 mL) and water (2 mL) under nitrogen. The mixture was reacted at 80° C. overnight. The reaction was quenched by addition of water and extracted with DCM (3×). The combined organic layer was washed with water, brine, dried (Na$_2$SO$_4$), filtered and concentrated under reduced pressure. The crude solid was purified by column chromatography (SiO$_2$, eluent: DCM/heptane 2/1). Compound 2401 (490 mg, 98%) was obtained as a yellow solid. M+H=600.3. $\lambda_{max}$ (ethyl acetate)=435 nm, ε=17700 and 455 nm, ε=15600. λ(em) (ethyl acetate) 489 nm and 516 nm.

7. 5,11-diphenylisochromeno[6,5,4-mna]xanthene-1,3-dione (2456)

To a solution of compound 2401 (1.20 g, 2.00 mmol) in tBuOH (60 mL) and 1,4-dioxane (15 mL) was added powder KOH (1.12 g, 20.00 mmol). The mixture was refluxed for 4 h. The yellow solution became reddish after a few minutes. The solution was cooled to room temperature and poured into AcOH (60 mL). After 2 minutes, 2 N aqueous HCl (300 mL) was added. The orange precipitate was collected by filtration, first washed with water then with heptane and Et2O to remove most of the unreacted starting material and 2,6-diisopropylaniline. The precipitate was stirred in refluxing AcOH (70 mL) for 10 minutes and concentrated. The residue was coated on silica gel and purified by column chromatography (SiO2, eluent: DCM/Heptane 2/1 to remove remaining starting material then with DCM/Heptane 4/1 to 1/0). Compound 2456 (40 mg, 41%) was obtained as an orange solid. Fractions containing starting material 2401 were combined and purified by column chromatography (SiO2, eluent: DCM/Heptane 2/1) to give pure recovered compound 2401 (255 mg, 21%).

8. Mixture of 6,16-diphenyl-8H-benzo[3,4]isochromeno[7,8,1-def]benzo[4,5]imidazo[1,2-b]isoquinolin-8-one and 5,15-diphenyl-7H-benzo[3,4]isochromeno[7,8,1-def]benzo[4,5]imidazo[2,1-a]isoquinolin-7-one (2441)

A mixture of 2456 (30 mg, 0.068 mmol) and o-phenylenediamine (36.8 mg, 0.34 mmol) in AcOH (10 mL) and 1,4-dioxane (5 mL) was refluxed for 6 h. The yellow solution became red. The mixture was cooled to room temperature and concentrated. The red solid obtained was triturated in MeOH (50 mL), collected by filtration on a glass filter, washed again with MeOH to remove excess of o-phenylenediamine and some other impurities then washed with heptane and dried under vacuum. Compound 2441 (mixture of isomers, 30 mg, 86%) was obtained as an orange-red solid. M+H=513.6. $\lambda_{max}$ (chloroform)=461 nm, ε=27400 and 488 nm, ε=29800. λ(em) (ethyl acetate) 502 nm and 535 nm.

See also FIGS. 3*b*/3*c* (2441) and 4*a* (101 (2441)).
Synthesis of 2442 (Mixture of Isomers):

1. 2-(2,6-diisopropylphenyl)-5,11-diphenoxy-1H-xantheno[2,1,9-def]isoquinoline-1,3(2H)-dione (2436)

A mixture of 2404 (2.0 g, 3.3 mmol), phenol (10.0 g, 16.5 mmol) and Cs2CO3 (6.4 g, 19.8 mmol) in degased 1,4-dioxane (1560 mL) was stirred at 90° C. under nitrogen for 1 h. Then, a mixture of Cu(I)I (314 mg, 1.65 mmol) and N,N-dimethylglycine (510 mg, 495 mmol) in 1,4-dioxane (4 mL) was added and the reaction mixture was stirred at 90° C. under nitrogen overnight. The mixture was cooled to room temperature and the solvent removed under reduced pressure. The residue was dissolved in DCM and SiO2 was added. The DCM was removed under reduced pressure and the product coated on silica was poured on top of a column chromatography for purification (SiO2, eluent: DCM/heptane 1/1). The compound was washed with hot heptane in a glass filter and dried under vacuum. Compound 2436 (1.0 g, 48%) was obtained as a yellow solid.

2. 5,11-diphenoxyisochromeno[6,5,4-mna]xanthene-1,3-dione (2457)

To a solution of compound 2436 (390 mg, 0.62 mmol) in tBuOH (20 mL) and 1,4-dioxane (5 mL) was added powder KOH (348 mg, 6.20 mmol). The mixture was refluxed for 4 h. The yellow solution became reddish after a few minutes. The solution was cooled to room temperature and poured into AcOH (50 mL). After 2 minutes, 2 N aqueous HCl (150 mL) was added. The orange precipitate was collected by filtration, first washed with water then with heptane and Et$_2$O to remove most of the unreacted starting material 2436 and 2,6-diisopropylaniline. The precipitate was stirred in refluxing AcOH (50 mL) for 10 minutes and concentrated. The residue was coated on silica gel and purified by column chromatography (SiO$_2$, eluent: DCM/Heptane 2/1 to remove remaining starting material then with DCM/Heptane 4/1 to 1/0). Compound 2457 (135 mg, 46%) was obtained as an orange solid.

3. Mixture of 6,16-diphenoxy-8H-benzo[3,4]isochromeno[7,8,1-def]benzo[4,5]imidazo[1,2-b]isoquinolin-8-one and 5,15-diphenoxy-7H-benzo[3,4]isochromeno[7,8,1-def]benzo[4,5]imidazo[2,1-a]isoquinolin-7-one (2442)

A mixture of 2457 (135 mg, 0.286 mmol) and o-phenylenediamine (36.8 mg, 0.34 mmol) in AcOH (50 mL) and 1,4-dioxane (15 mL) was refluxed for 6 h. The yellow solution became red. The mixture was cooled to room temperature and concentrated. The red solid obtained was triturated in MeOH (60 mL), collected by filtration on a glass filter, washed again with MeOH to remove excess of o-phenylenediamine and some other impurities then washed with heptane and dried under vacuum. Compound 2442 (mixture of isomers, 132 mg, 85%) was obtained as an orange-red solid. M+H=545.2. $\lambda_{max}$ (chloroform)=463 nm, ε=40500 and 485 nm, ε=47200. λ(em) (ethyl acetate) 508 nm and 540 nm.

See also FIGS. 3b/3c (2442) and 4a (102 (2442)).
Synthesis of 2464 (Mixture of Isomers):

1. 2-(2,6-diisopropylphenyl)-5-bromo-11-phenoxy-1H-xantheno[2,1,9-def]isoquinoline-1,3(2H)-dione (2405)

A mixture of 2404 (1.4 g, 2.31 mmol), phenol (1.2 g, 12.75 mmol) and K$_2$CO$_3$ (2.2 g, 15.92 mmol) in NMP (60 mL) was stirred at 90° C. under nitrogen overnight. Then, the contents of the flask were poured into a cold 20% acetic acid solution in water. After 5 minutes, 2 N aqueous HCl was added and stirred for 10 minutes and the precipitated solid was filtered, washed neutral with warm water and vacuum dried at 60° C. The residue was coated on silica gel and purified by column chromatography (SiO$_2$, eluent: DCM/Heptane 1/1 to 2/1). Compound 2405 (1.1 g, 76%) was obtained as a yellow solid.

2. 2-(2,6-diisopropylphenyl)-11-phenoxy-1H-xantheno[2,1,9-def]isoquinoline-1,3(2H)-dione (2389)

To a clear solution of compound 2405 (600 mg, 0.97 mmol) in THF (80 mL) and MeOH (10 mL) under nitrogen was added 10% Pd/C (100 mg) and the reaction was placed under hydrogen atmosphere with a balloon. The mixture was stirred at 30° C. overnight and then filtered over Celite. The crude solid was purified by column chromatography (SiO$_2$, eluent: toluene/DCM 3/2). Compound 2389 (540 mg, 98%) was obtained as a yellow solid.

3. 11-phenoxyisochromeno[6,5,4-mna]xanthene-1,3-dione (2464)

To a solution of compound 2389 (2.0 g, 3.71 mmol) in tBuOH (110 mL) and 1,4-dioxane (30 mL) was added powder KOH (2.1 g, 37.10 mmol). The mixture was refluxed for 1 h. The yellow solution became orange after a few minutes. The solution was cooled to room temperature and poured into AcOH (100 mL). After 2 minutes, 2 N aqueous HCl (300 mL) was added. The orange precipitate was collected by filtration, first washed with water then with heptane and Et$_2$O to remove most of the unreacted starting material 2389 and 2,6-diisopropylaniline. The precipitate was stirred in refluxing AcOH (70 mL) for 10 minutes and concentrated. The residue was coated on silica gel and purified by column chromatography (SiO$_2$, eluent: DCM/Heptane 2/1 to remove remaining starting material then with DCM/Heptane 4/1 to 1/0). Compound 2646 (600 mg, 42%) was obtained as an yellow-orange solid. Fractions containing starting material 2389 were combined and purified by column chromatography (SiO$_2$, eluent: DCM/Heptane 2/1) to give pure recovered compound 2646 (600 mg, 42%).

4. Mixture of 16-phenoxy-8H-benzo[3,4]isochromeno[7,8,1-def]benzo[4,5]imidazo[1,2-b]isoquinolin-8-one and 5-phenoxy-7H-benzo[3,4]isochromeno[7,8,1-def]benzo[4,5]imidazo[2,1-a]isoquinolin-7-one (2463)

A suspension of 2464 (600 mg, 1.58 mmol) and o-phenylenediamine (853 mg, 7.89 mmol) in AcOH (100 mL) and 1,4-dioxane (20 mL) was refluxed for 16 h. The yellow suspension became an orange clear solution then an orange precipitate was formed. The mixture was cooled to room temperature and concentrated. The red solid obtained was triturated in MeOH (70 mL), collected by filtration on a glass filter, washed again with MeOH (4×50 mL) to remove excess of o-phenylenediamine and some other impurities then washed with heptane and dried under vacuum. Compound 2463 (mixture of isomers, 680 mg, 93%) was obtained as an orange solid. M+H=452.9.2. $\lambda_{max}$ (chloroform)=455 nm, ε=30900 and 481 nm, ε=33700. λ(em) (ethyl acetate) 496 nm and 529 nm.

Figure 5A:
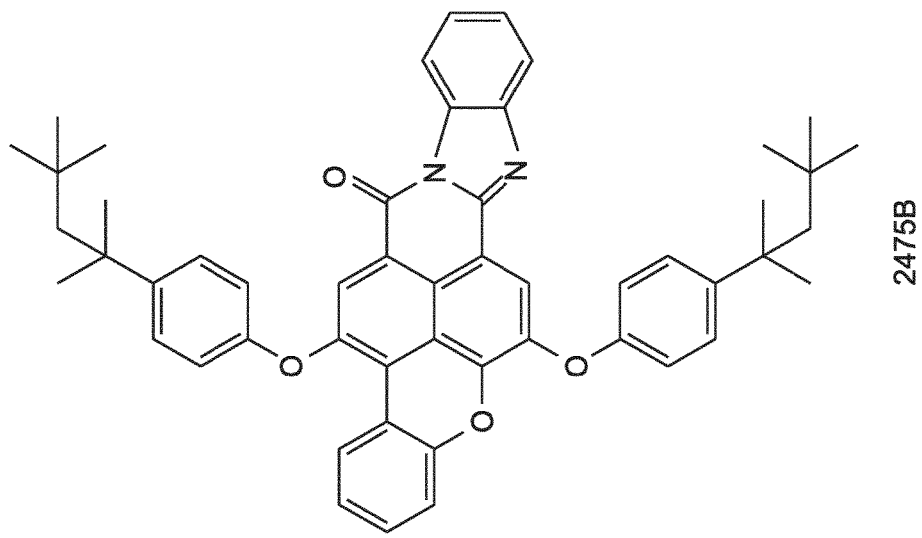
FIGS. 5a-5b depicts phosphors 2485A/2485B and 2475A/2475B, respectively.
Figure 5A:
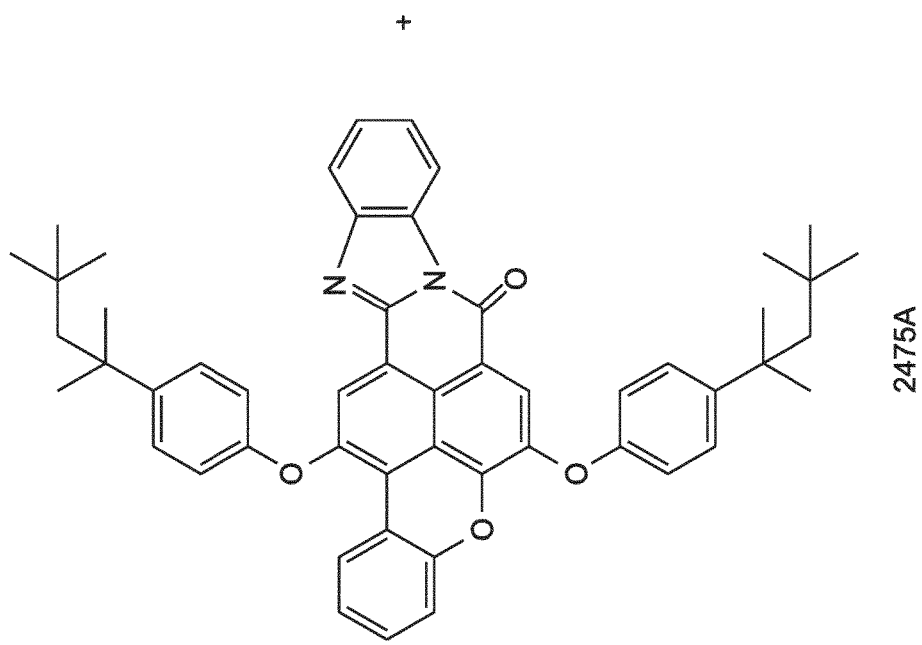
Figure 5B:
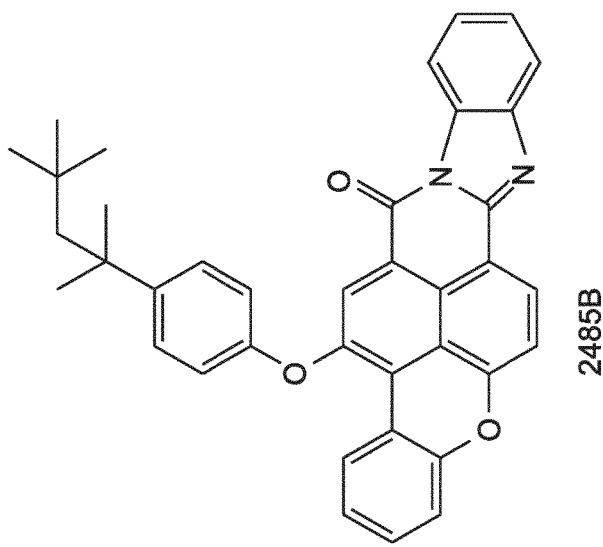
Figure 5B:
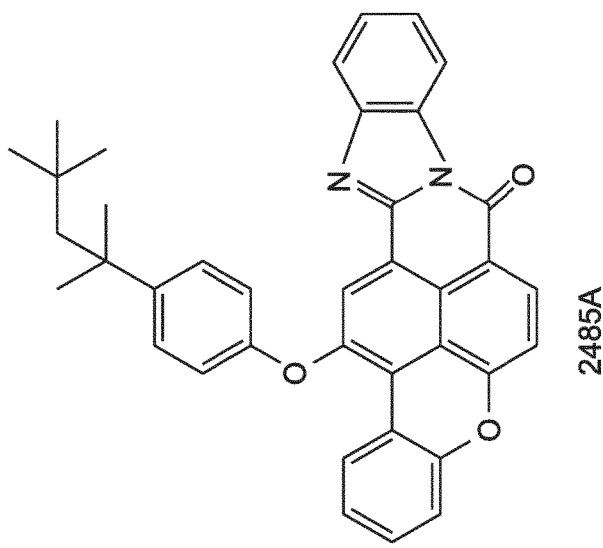

See also FIGS. 3b/3c (2463) and 4a (111 (2463)).
Further materials were made, of which the structure formulas are indicated in FIGS. 5a and 5b.

Synthesis of a Mixture of 6,16-bis(4-(2,4,4-trimethylpentan-2-yl)phenoxy)-8H-benzo[3,4]isochromeno[7,8,1-def]benzo[4,5]imidazo[1,2-b]isoquinolin-8-one and 5,15-bis(4-(2,4,4-trimethylpentan-2-yl)phenoxy)-7H-benzo[3,4]isochromeno[7,8,1-def]benzo[4,5]imidazo[2,1-a]isoquinolin-7-one (2475)

This compound was made in the same manner as described for the synthesis of 2442, but replacing phenol by 4-(2,4,4-trimethylpentan-2-yl)phenol.

Compound 2475 was obtained as an orange-red solid. M+H=769.4. $\lambda_{max}$ (ethyl acetate)=456 nm, ε=23900 and 479 nm, ε=27700. λ (em) (ethyl acetate) 510 nm and 542 nm.

Separation of 2475 into its Isomers 6,16-bis(4-(2,4,4-trimethylpentan-2-yl)phenoxy)-8H-benzo[3,4]isochromeno[7,8,1-def]benzo[4,5]imidazo[1,2-b]isoquinolin-8-one (2475A) and 5,15-bis(4-(2,4,4-trimethylpentan-2-yl)phenoxy)-7H-benzo[3,4]isochromeno[7,8,1-def]benzo[4,5]imidazo[2,1-a]isoquinolin-7-one (2475B)

Mixture 2475 (300 mg) was poured on top of a chromatography column (SiO$_2$). Elution with DCM/Heptane 2/1 gave a first fraction containing 2475A (yellow DCM solution). After evaporation 175 mg of 2475A was obtained as orange solid. λ (em) (ethyl acetate) 510 nm. Further elution afforded a fraction containing 2475B (orange DCM solution). After evaporation 100 mg of 2475B was obtained as a red solid. λ (em) (ethyl acetate) 561 nm.

Synthesis of a Mixture of 16-(4-(2,4,4-trimethylpentan-2-yl)phenoxy)-8H-benzo[3,4]isochromeno[7,8,1-def]benzo[4,5]imidazo[1,2-b]isoquinolin-8-one and 5-(4-(2,4,4-trimethylpentan-2-yl)phenoxy)-7H-benzo[3,4]isochromeno[7,8,1-def]benzo[4,5]imidazo[2,1-a]isoquinolin-7-one (2485)

This compound was made in the same manner as described for the synthesis of 2463, but replacing phenol by 4-(2,4,4-trimethylpentan-2-yl)phenol.

Compound 2485 was obtained as an orange solid. M+H=574.8. $\lambda_{max}$ (ethyl acetate)=448 nm, ε=27000 and 473 nm, ε=29500. λ (em) (ethyl acetate) 498 nm and 531 nm.

Separation of 2485 into its Isomers 16-(4-(2,4,4-trimethylpentan-2-yl)phenoxy)-8H-benzo[3,4]isochromeno[7,8,1-def]benzo[4,5]imidazo[1,2-b]isoquinolin-8-one (2485A) and 5-(4-(2,4,4-trimethylpentan-2-yl)phenoxy)-7H-benzo[3,4]isochromeno[7,8,1-def]benzo[4,5]imidazo[2,1-a]isoquinolin-7-one (2485B)

Mixture 2485 (330 mg) was poured on top of a chromatography column (SiO$_2$). Elution with DCM/Heptane 3/1 gave a first fraction containing 2485A (yellow DCM solution). After evaporation 195 mg of 2485A was obtained as an orange solid. $\lambda_{max}$ (ethyl acetate)=448 nm, ε=31500 and 473 nm, ε=32500. λ (em) (ethyl acetate) 498 nm and 530 nm.

Further elution with DCM afforded a fraction containing 2485B (orange DCM solution). After evaporation 120 mg of 2485B was obtained as a red solid. $\lambda_{max}$ (ethyl acetate)=475 nm, ε=31500 and 473 nm, ε=18100. λ (em) (ethyl acetate) 547 nm.

The lifetime of 2410 and other systems in a PET (polyethylene terephthalate) film was tested by measuring the lifetime under illumination with blue light at 0.5-7 W/cm$^2$ at 60° C. The concentration and the thickness of the layers were set so that the transmission of blue light was 90%.

The lifetime is determined as 10% luminescence reduction extrapolated to the conditions for a TLED (0.016 W/cm$^2$ blue and a temperature of 60° C. in air) assuming a linear dependence of the decay rate on the flux density. In the case of F083 a lifetime of about 100 hours was estimated while new compound 2410 showed a lifetime of about 12500 hours. This means an increase in lifetime of about 125 times.

Lifetime of organic yellow emitting molecules in a PET matrix (in hours at which 10% has bleached at an exposure of 0.016 W/cm$^2$ blue and a temperature of 60° C. in air), see table 1:

TABLE 1

| Lifetime measurements | |
|---|---|
| Compound | Lifetime (hrs) |
| F083 | 50-200 |
| F170 | 150-400 |
| Solvent yellow 98 | 400-650 |
| 2410A + 2410B | 12500 |
| 2441A + 2441B | 12500 |

TABLE 1-continued

| Lifetime measurements | |
|---|---|
| Compound | Lifetime (hrs) |
| 2442A + 2442B | 17000 |
| 2463A + 2463B | 21000 |
| 2475A + 2475B | 13000 |
| 2485A + 2485B | 18000 |

It appears that phenoxy substituted compounds have a longer lifetime. Further, it appears that G2 substitution may have an even stronger lifetime enhancement effect than G7 substituted compounds.

Matrices than PET (or PET analogues) provide in general worse results. PETG and PET especially provide stable luminescent systems.

Examples of White Blends

Example 1

Figure 4B:
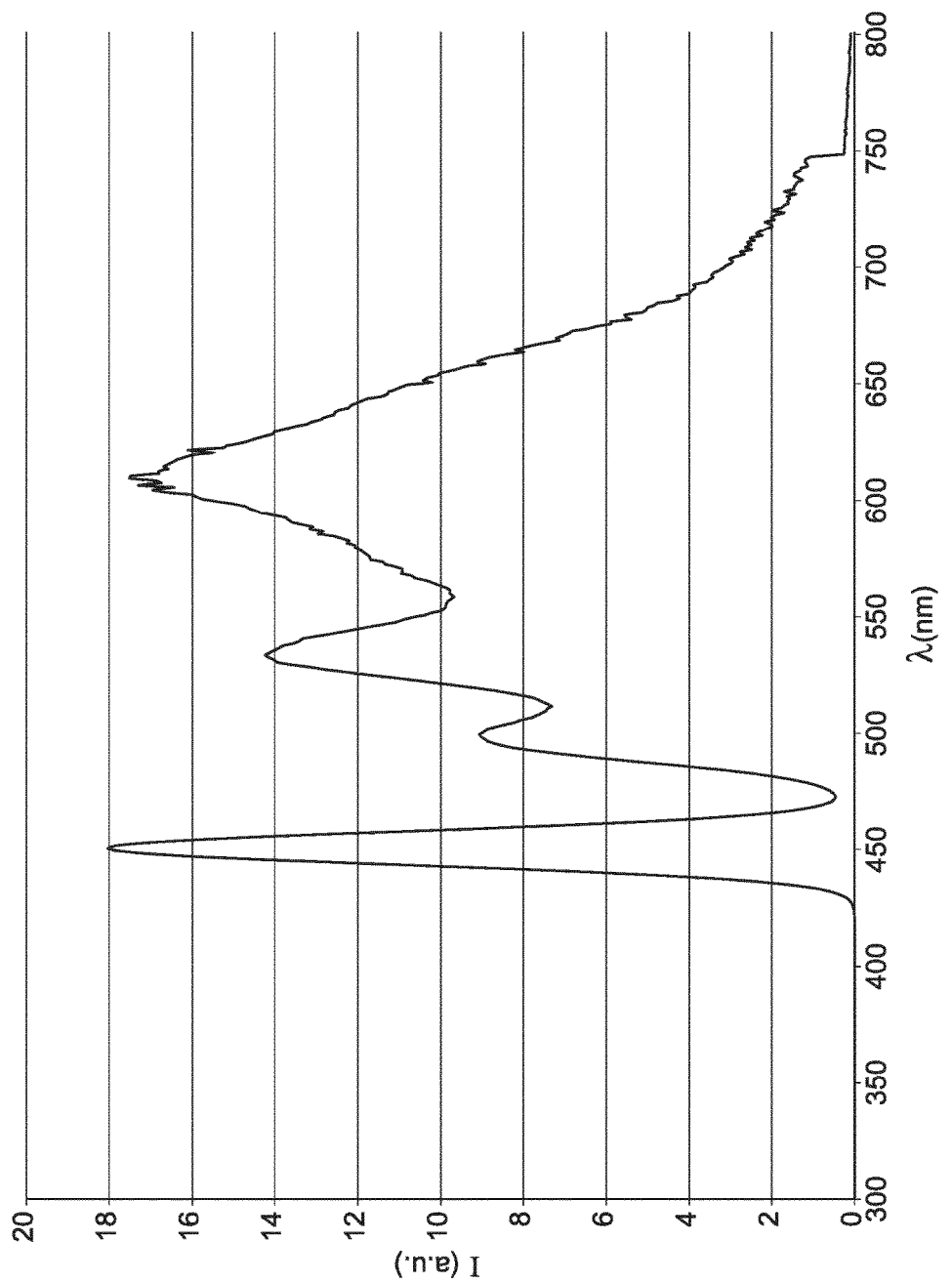
FIGS. 4b-4f depict white light luminescence spectra using a blue LED as excitation source, and further the luminescent material in combination with another organic luminescent material (b), a quantum dot material (c) or a red LED (d) (see also the table 2 at the end of the experiments)

Emission of various organic molecules excited by blue LED can be combined to produce white light. Herein, the emission from the molecules depicted in FIG. 3a (material 2410, see FIGS. 3a/4a) and N,N'-Bis(2,6-diisopropylphenyl)-1,6,7,12-tetraphenoxyperylene-3,4:9,10-tetracarboxdiimide; CAS nr. 123174-58-3, also known as F305 (from BASF)), were combined with blue light to obtain white light with a spectrum shown in FIG. 4b. Such a white light can be produced showing the following values shown in the table below.

Example 2

Figure 4C:
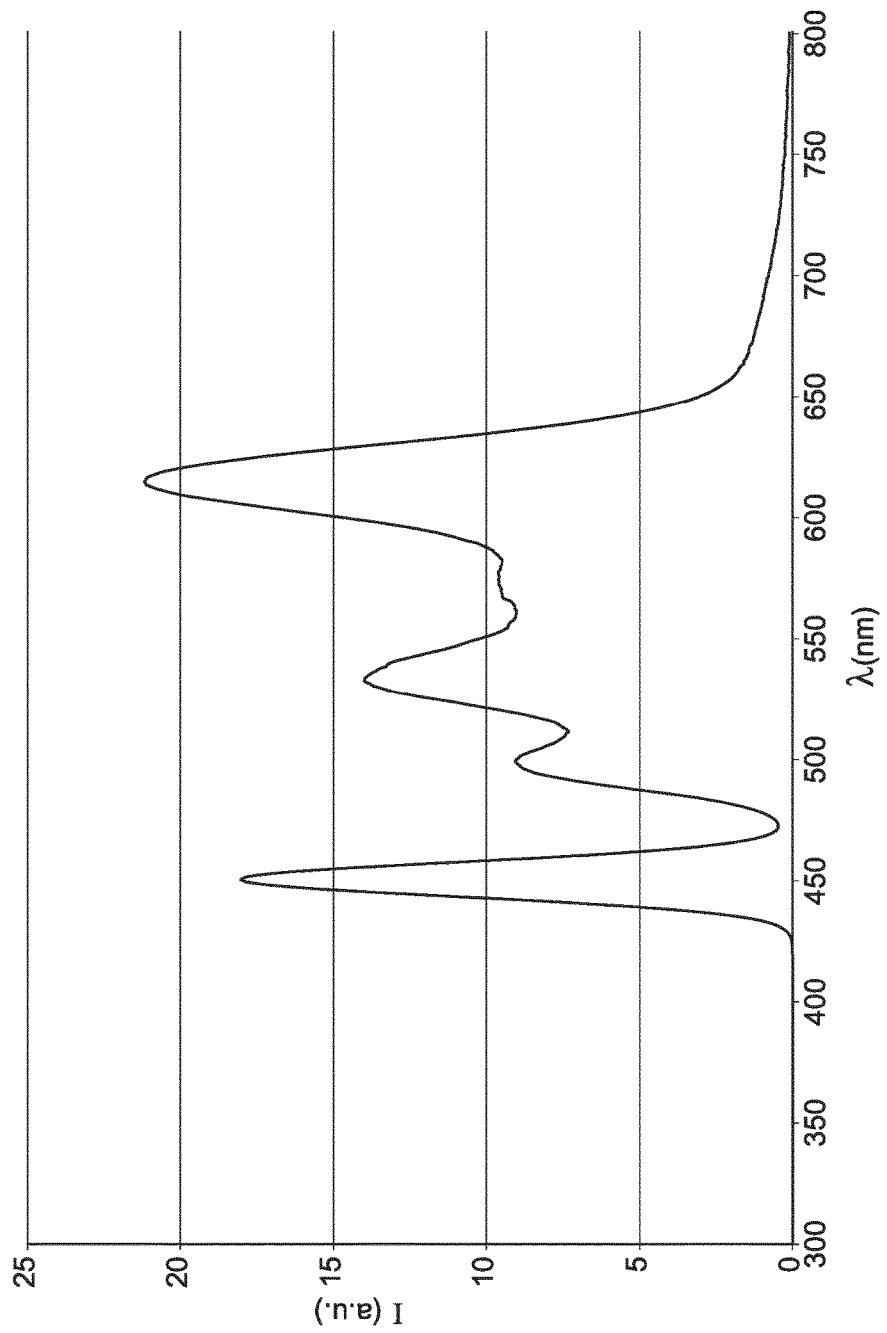

In this example the emission from the molecules depicted in FIG. 3a (material 2410, see FIG. 3a/4a) is combined with blue light and also with emission from a quantum dot with a emission maximum at 615 nm to obtain white light with a spectrum shown in FIG. 4c, and with values as shown in the table below.

Example 3

Figure 4D:
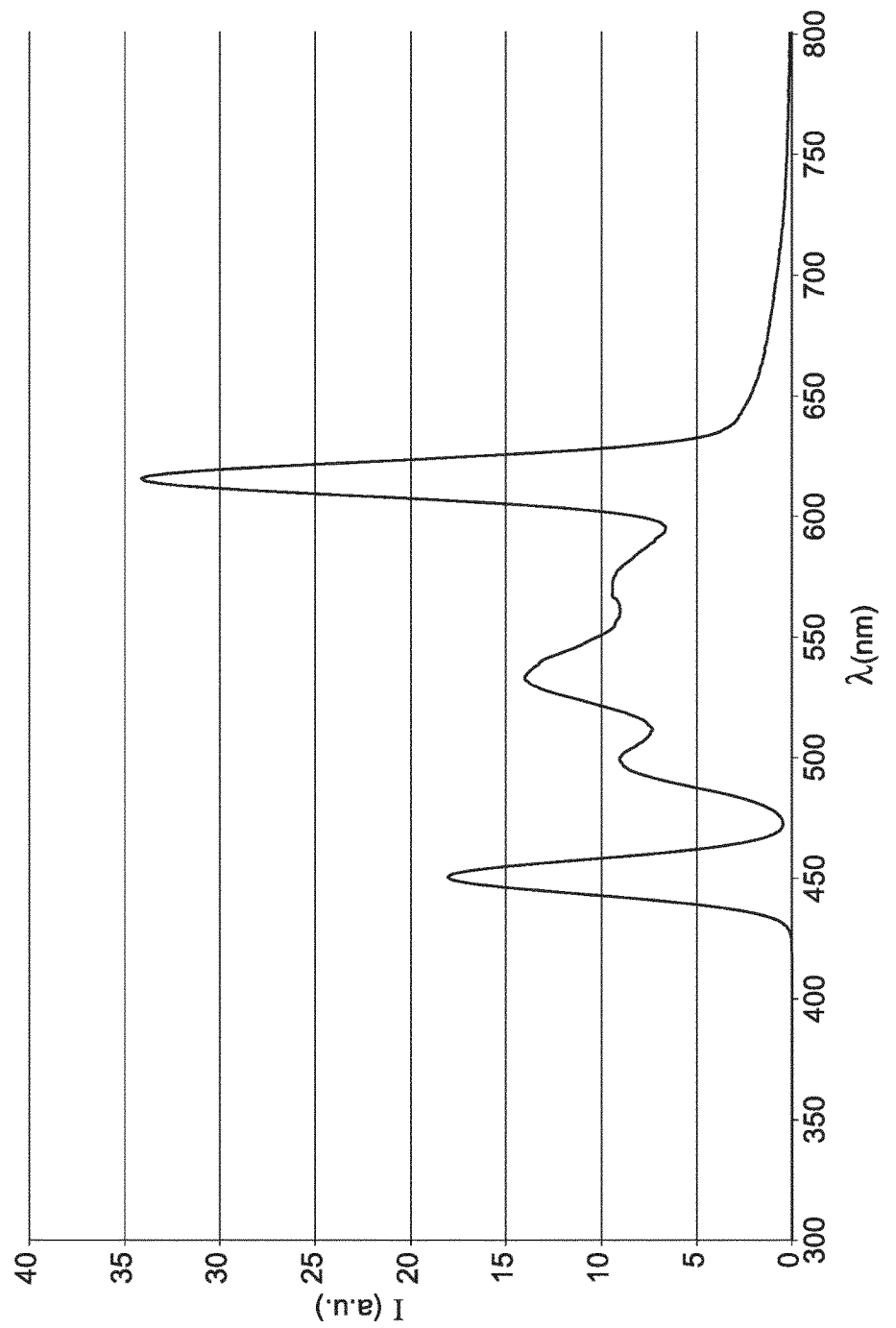

In this example the emission from the molecules depicted in FIG. 3a (material 2410, see FIG. 3a/4a) is combined with blue light and also with emission from a red LED with a emission maximum at 615 nm to obtain white light with a spectrum shown in FIG. 4d, and with values as shown in the table below.

Example 4

Figure 4E:
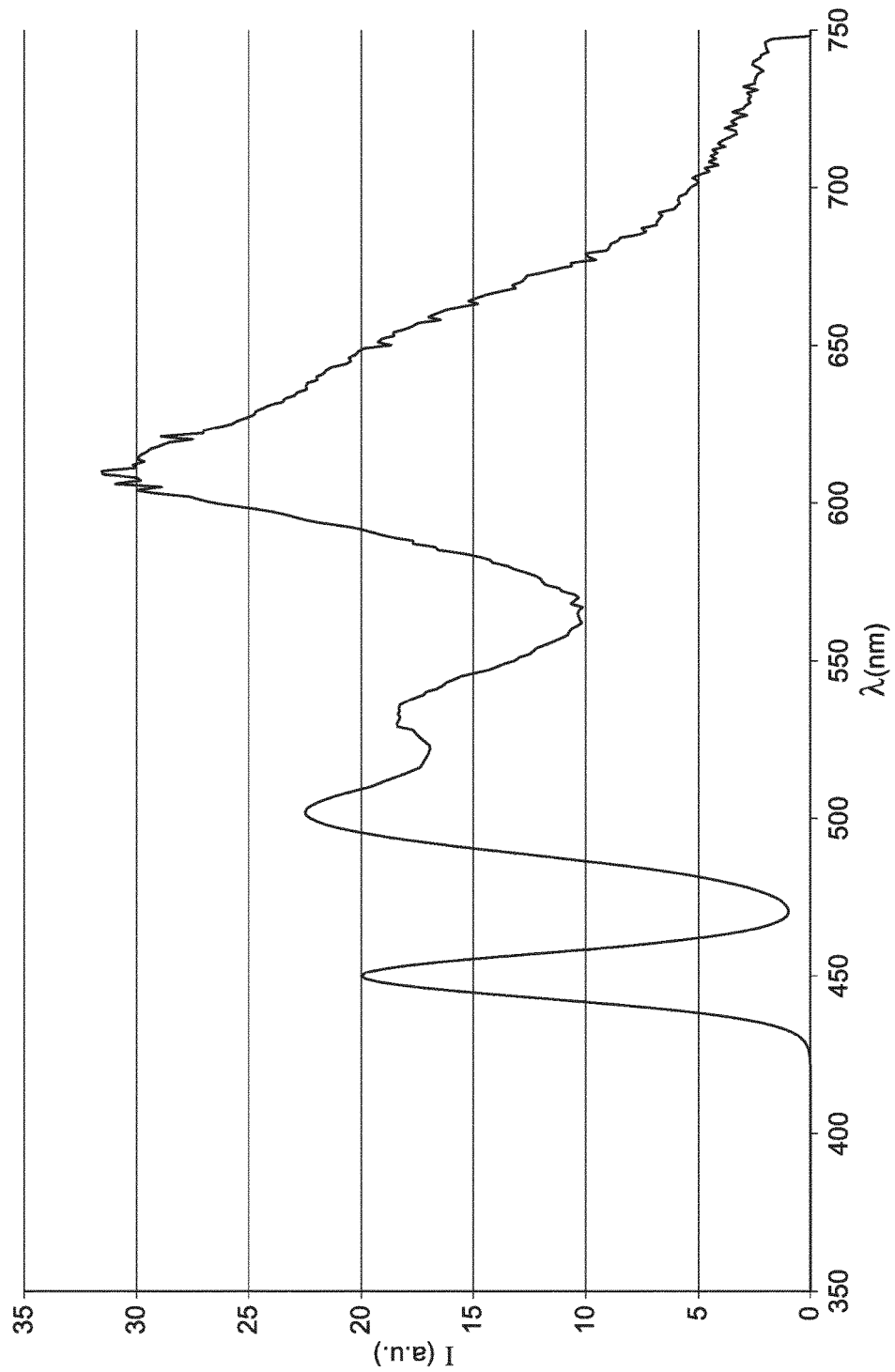

In this example the emission from the molecules depicted in FIG. 3a (material 2441, see FIG. 3c/4a) is combined with blue light and also with emission from a red luminescent material F305 to obtain white light with a spectrum shown in FIG. 4e, and with values as shown in the table below.

Example 5

Figure 4F:
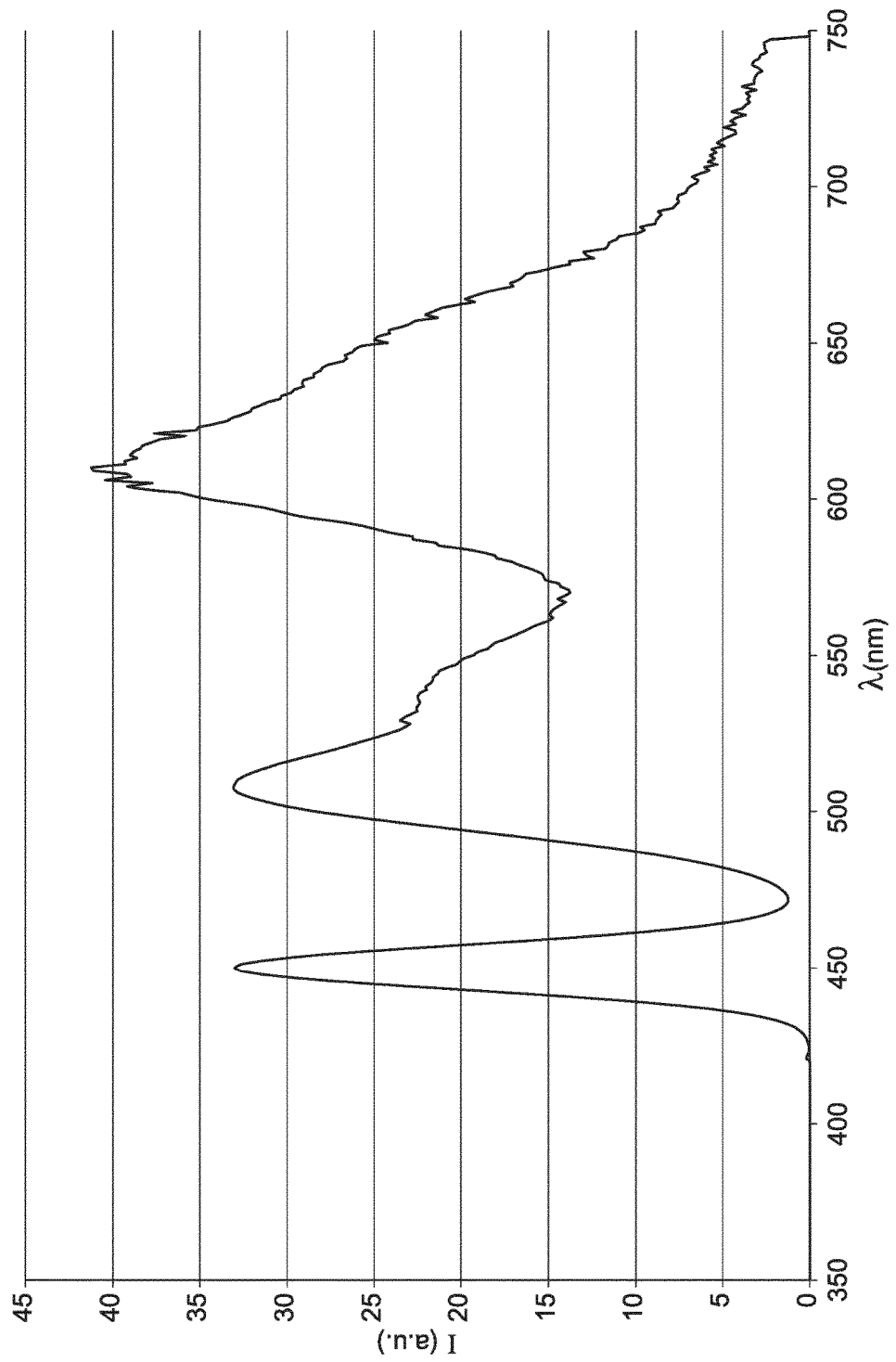

In this example the emission from the molecules depicted in FIG. 3a (material 2442, see FIGS. 3c/4a) is combined with blue light and also with emission from a red luminescent material F305 to obtain white light with a spectrum shown in FIG. 4f, and with values as shown in the table below.

TABLE 2

White blends

|  | Lumen equivalent (Lm/W) | CCT (K) | CRI | R9 |
| --- | --- | --- | --- | --- |
| Example 1 (blue + 2410 + F305) | 311 | 3550 | 92 | 11 |
| Example 2 (blue + 2410 + QDs) | 350 | 3665 | 92 | 30 |
| Example 3 (blue + 2410 + Red LED) | 350 | 3700 | 90 | 44 |
| Example 4 (blue + 2441 + F305) | 290 | 3300 | 84 | 94 |
| Example 5 (blue + 2442 + F305) | 290 | 3500 | 85 | 93 |

Hence, referring to—amongst others—FIGS. 3A, 3b(C), 3C(A), 3C(B), 5A, 5B, the invention also provides in an embodiment luminescent material comprising a combination of at least two organic phosphors selected from the group consisting of (combinations): (i) 2410A+2410B, (ii) 2441A+2441B, (iii) 2442A+2442B, (iv) 2463A+2463B, (v) 2475A+2475B, and (vi) 2485A+2485B. The phrase "2410A+2410B" and similar phrases refers to the combination of the isomers. Hence, the luminescent materials as described herein especially comprises a combination of two (related) isomers, and optionally more than one of such combination, such as e.g. a combination of 2410A+2410B and 2475A+2475B, etc. Hence, in embodiment the luminescent material comprises combinations of two isomers, (the combinations) selected from the above indicated six groups. The sets of isomers are depicted in the above mentioned drawings; the general formulas are amongst others indicated in FIG. 2A.

As indicated above, we found after separation of the two isomers from the mixture that the one derived from structure 2410A has excellent spectral properties in the yellow region and a high quantum yield, exceeding 0.9. The other isomer derived from 2410B exhibits an emission in the orange region with a relatively low quantum yield. Thus the use of the first isomer leads to lamps with higher efficiency. Especially in the case when the rather soluble derivates 2475 and 2485 (see FIGS. 5a-5b) are used, separation by column chromatography may be executed. In all cases the first fraction contains the derivative with good spectral properties and high quantum yield. After further elution the other isomer could be isolated.

Figure 6A:
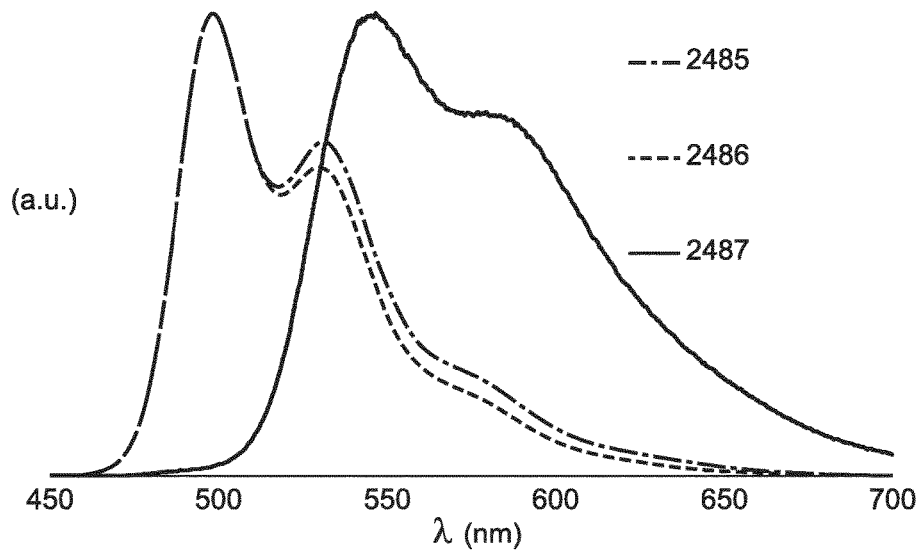
FIGS. 6a-6b show normalized luminescence spectra (at RT) of the phosphors of FIGS. 6a-6b in ethyl acetate of those materials (2486=2485A; 2487=2485B; 2485 is the mixture; 2504=2475A; 2505=2475B; 2475 is the mixture.
Figure 6B:
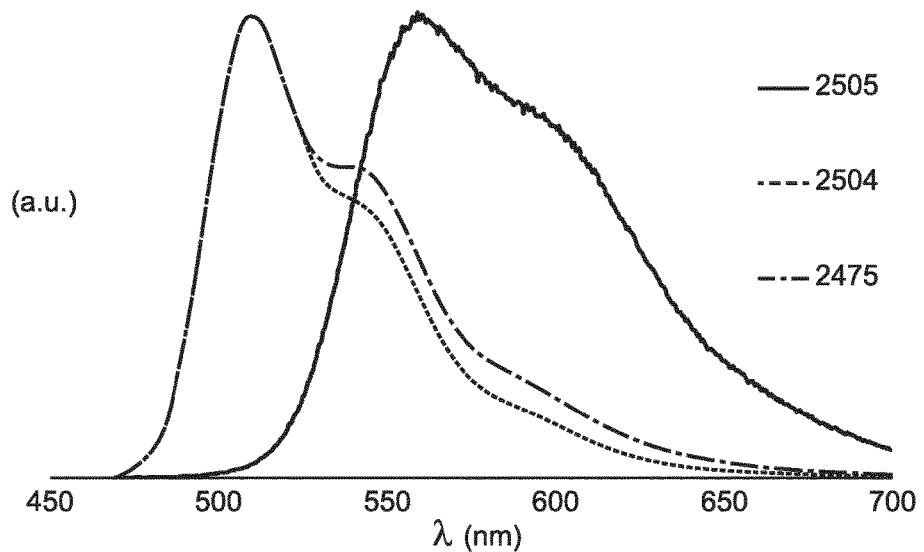

We separated mixture 2485 into isomers 2485A and 2485B. The first isomer that was isolated by column chromatography was 2485A. In order to determine the structure of 2485A exactly, a C—H 3 band coupling NMR spectrum was taken that showed such a coupling between the doublet of $H^B$ and the carbon of the carbonyl moiety. Thus derivatives of 2410A are the compounds that are obtained as first fraction from the chromatographic separation. In the same way mixture 2475 was separated in its two isomers by column chromatography (FIG. 5b). FIGS. 6a-6b show the normalized emission spectra of 2485, 2485A and 2485B and of 2475, 2475A and 2475B in ethyl acetate. Compounds 2485B and 2475B are clearly not yellow but orange emitters. Furthermore, the PLQE (photo luminescence quantum efficiency) of these range emitters (structure II, derived from 2410B) is rather low as shown in the table II. These values will of course also affect the PLQE of the mixtures 2475 and 2485.

TABLE II optical and lifetime data on mixtures and pure components

| Number | Structure | G2 | G7 | PLQE | Lifetime |
| --- | --- | --- | --- | --- | --- |
| 2485 | mix | $C_8H_{17}C_6H_4O$ | H | 0.68 | 11 Khr |
| 2485A | I (A) | $C_8H_{17}C_6H_4O$ | H | 0.90 | 17 Khr |
| 2485B | II (B) | $C_8H_{17}C_6H_4O$ | H | 0.46 | 18 Khr |
| 2475 | mix | $C_8H_{17}C_6H_4O$ | $C_8H_{17}C_6H_4O$ | 0.77 | 13 Khr |
| 2475A | I (A) | $C_8H_{17}C_6H_4O$ | $C_8H_{17}C_6H_4O$ | 0.90 | 10 Khr |
| 2475B | II (B) | $C_8H_{17}C_6H_4O$ | $C_8H_{17}C_6H_4O$ | 0.52 | 23 Khr |

The structures I (derived from 2410A) on the other hand have a good spectrum and a high quantum yield. We therefore suggest the use of the following organic phosphor isomers and its derivatives or similarities in phosphor converted LED applications as (green/yellow) emitters as defined by formula IA, wherein for instance G1-G12 are independently hydrogen, a linear or branched alkyl group or oxygen-containing alkyl group $C_nH_{2n+1}O_m$, n being an integer from 1 to 16 and m<n/2 or 0, fluorine, chlorine, or Y, OY or NRY. R being an alkyl or aryl group. D,E,I,L and M are H, F, Cl, a linear or branched alkyl group or oxygen-containing alkyl group $C_nH_{2n+1}O_m$, n being an integer from 1 to 16 and m<n/2 or 0; especially minimally two of these groups are hydrogen atoms. Especially, minimally 4 of the groups G1-G8 are hydrogen atoms. Further, one or more of G1-G12, especially one, may also contain a covalent link to a polymer backbone in case of incorporation in a polymer.

We tested the lifetime of the molecules in a PET (polyethylene terephthalate) film by measuring the lifetime under illumination with blue light at 4.1/W/cm2 at 60 C. The concentration and the thickness of the layer were set so that the transmission of blue light was 90%.

Figure 6C:
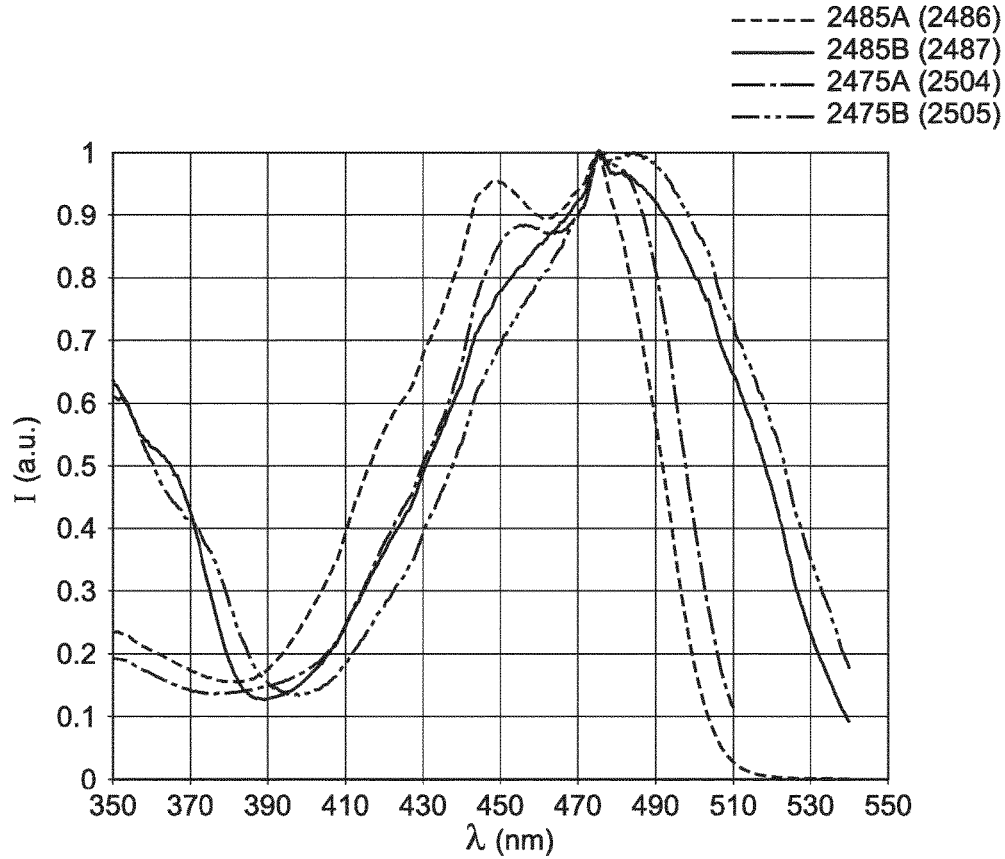
FIG. 6c shows the normalized excitation spectra (at RT) of these organic phosphors.

The lifetime is estimated as 10% reduction under conditions for a TLED (0.016 W/cm$^2$ blue and a temperature of 60° C. in air). In the case of F083 a lifetime of about 150 hours was estimated while compounds 2485A and 2475A showed a lifetime of more than 10000 hours. This means an increase in lifetime of about 60 times while having good spectral properties and high quantum yield. Normalized emission and excitation spectra of the 2485 and 2475 isomers are shown in FIGS. 6a-6c.

The invention claimed is:
1. A lighting device comprising (a) a light source configured to generate light source light, and (b) a light converter configured to convert at least part of the light source light into visible converter light, wherein the light converter comprises a matrix containing a luminescent material comprising at least an organic phosphor defined by formula IA, and optionally an organic phosphor defined by formula TB:

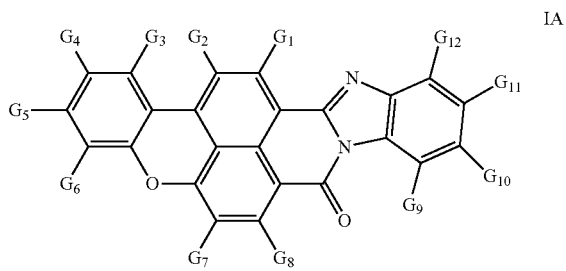

-continued

IB

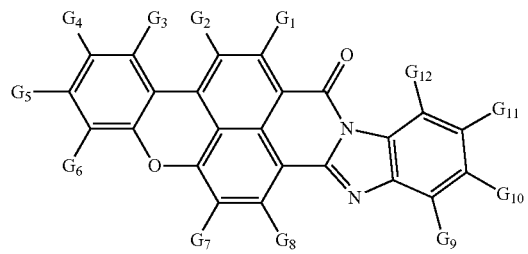

wherein G1-G12 are independently selected from hydrogen, halogen, R1, OR1, NHR1, and NR2R1, wherein R1 and R2 are independently selected from C1-C18alkyl, C6-C24aryl, and C6-C24heteroaryl, wherein optionally one or more of G1-G12 is covalently linked to the matrix, and wherein when the organic phosphor defined by formula IB is available in the luminescent material, the phosphor defined by formula IB and the phosphor defined by formula IA have a molar ratio of 1B/1A ≤0.1, wherein at least four of G1-G12 for the organic phosphor IA independently are H, and wherein independently one or more of G2 and G7 for the organic phosphor IA comprise R1 or OR1, with R1 being defined by formula II:

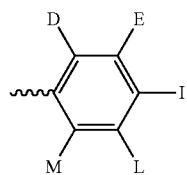

II wherein D, E, I, L and M are independently selected from hydrogen, halogen, R3, OR3, NHR3, and NR4R3, and wherein R3 and R4 are independently selected from C1-C18alkyl, C6-C24aryl, and C6-C24heteroaryl.

2. The lighting device according to claim 1, wherein at least ten of G1-G12 independently are H.

3. The lighting device according to claim 1, wherein independently one or more of G2 and G7 for the organic phosphor IA comprise R1 or OR1 and wherein R1 comprises a group defined by formula II:

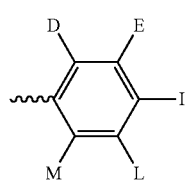

II wherein D, E, I, L and M are H, and wherein at least four of G1, G3, G4, G5, G6, G8, G9, G10, G11 and G12 independently are H.

4. The lighting device according to claim 3, wherein at least eight of G1, G3, G4, G5, G6, G8, G9, G10, G11 and G12 independently are H.

5. The lighting device according to claim 1, wherein the luminescent material comprising a combination of at least two different organic phosphors defined by formulas IA and IA' and optionally at least four different organic phosphors defined by formulas IA, IB, IA' and IB':

IA

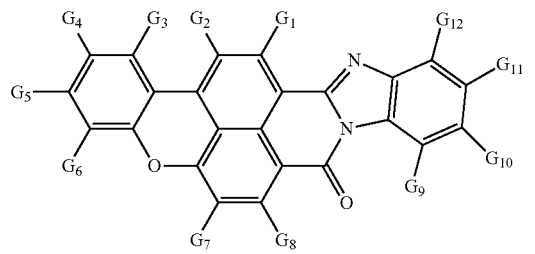

IA¹

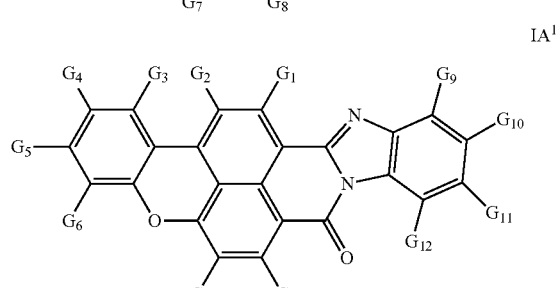

IB

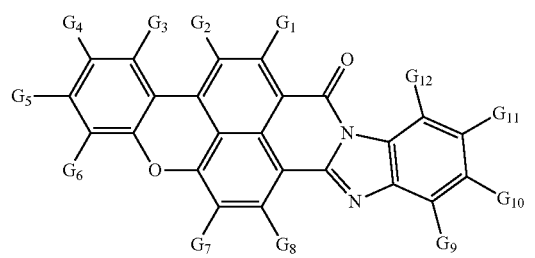

IB¹

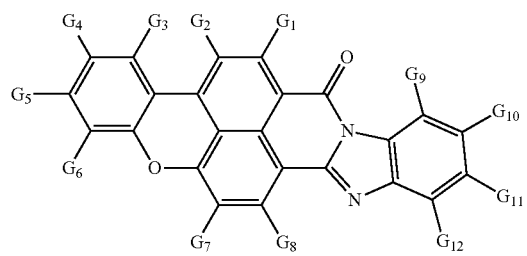

wherein G1-G12 are as defined above, with a molar ratio of IB/1A ≤0.1 and a molar ratio of IB'/1A'≤0.5.

6. The lighting device according to claim 1, wherein the matrix comprises a polymeric material.

7. The lighting device according to claim 1, wherein the matrix comprises an aromatic polyester or a copolymer thereof.

8. The lighting device according to claim 1, wherein one or more of G1, G2, G3, G4, G5, G6, G7, G8, G9, G10, G11, and G12 comprise a covalent link with the matrix.

9. A light converter comprising a matrix containing a luminescent material according to claim 1.

10. A lighting device comprising (a) a light source configured to generate light source light, and (b) a light converter configured to convert at least part of the light source light into visible converter light, wherein the light converter comprises a matrix containing a luminescent material comprising at least an organic phosphor defined by formula IA, and optionally an organic phosphor defined by formula IB:

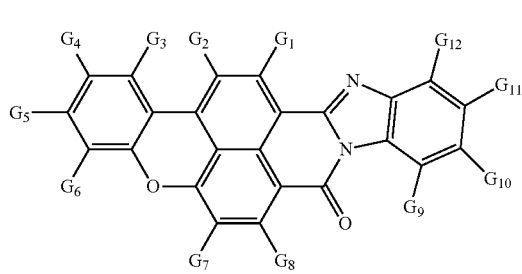

IA

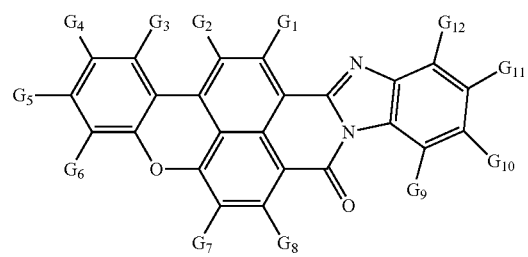

IA

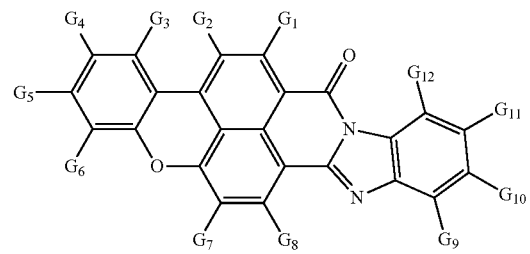

IB

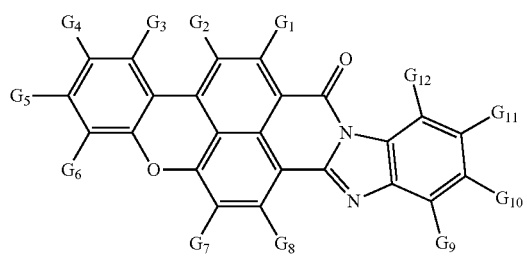

IB wherein G1-G12 are independently selected from hydrogen, halogen, R1, OR1, NHR1, and NR2R1, wherein R1 and R2 are independently selected from C1-C18alkyl, C6-C24aryl, and C6-C24heteroaryl, wherein optionally one or more of G1-G12 is covalently linked to the matrix, and wherein when the organic phosphor defined by formula IB is available in the luminescent material, the phosphor defined by formula IB and the phosphor defined by formula IA have a molar ratio of 1B/1A ≤0.1, wherein one or more of G1-G12 of the organic phosphor IA are independently selected from R1, OR1, NHR1, and NR2R1, wherein one or more of R1 and R2 independently comprise a group defined by formula II:

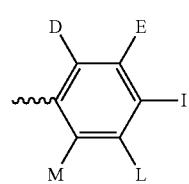

II wherein D, E, I, L and M are independently selected from hydrogen, halogen, R3, OR3, NHR3, and NR4R3, and wherein R3 and R4 are independently selected from C1-C18alkyl, C6-C24aryl, and C6-C24heteroaryl.

11. The lighting device according to claim 10, wherein at least two of D, E, I, L and M are H.

12. A luminescent material comprising at least an organic phosphor defined by formula IA and optionally also an organic phosphor defined by formula IB:

wherein G1-G12 are independently selected from hydrogen, halogen, R1, OR1, NHR1, and NR2R1, wherein R1 and R2 are independently selected from C1-C18alkyl, C6-C24aryl, and C6-C24heteroaryl, and wherein when the organic phosphor defined by formula IB is available in the luminescent material, the phosphor defined by formula IB and the phosphor defined by formula IA have a molar ratio of 1B/1A ≤0.1, and wherein one or more of G2 and G7 comprises independently a group selected from the group consisting of R1, OR1, NHR1, and NR2R1, and wherein at least four of G1-G12 for the organic phosphor IA independently are H, and wherein independently one or more of G2 and G7 for the organic phosphor IA comprise R1 or OR1, with R1 being defined by formula II;

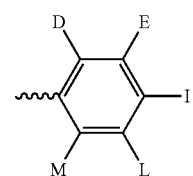

II wherein D, E, I, L and M are independently selected from hydrogen, halogen, R3, OR3, NHR3, and NR4R3, and wherein R3 and R4 are independently selected from C1-C18alkyl, C6-C24aryl, and C6-C24heteroaryl,
the luminescent material, comprising an organic phosphor selected from the group consisting of
6,16-diphenyl-8H-benzo[3,4]isochromeno[7,8,1-def]benzo[4,5]imidazo[1,2-b]isoquinolin-8-one;
6,16-diphenoxy-8H-benzo[3,4]isochromeno[7,8,1-def]benzo[4,5]imidazo[1,2-b]isoquinolin-8-one;
16-phenoxy-8H-benzo[3,4]isochromeno[7,8,1-def]benzo[4,5]imidazo[1,2-b]isoquinolin-8-one;
6,16-bis(4-(2,4,4-trimethylpentan-2-yl)phenoxy)-8H-benzo[3,4]isochromeno[7,8,1-def]benzo[4,5]imidazo[1,2-b]isoquinolin-8-one; and
16-(4-(2,4,4-trimethylpentan-2-yl)phenoxy)-8H-benzo[3,4]isochromeno[7,8,1-def]benzo[4,5]imidazo[1,2-b]isoquinolin-8-one.

13. The luminescent material according to claim 12, comprising 6,16-diphenyl-8H-benzo[3,4]isochromeno[7,8,1-def]benzo[4,5]imidazo[1,2-b]isoquinolin-8-one.

* * * * *